United States Patent
Blanchard et al.

(10) Patent No.: US 11,834,489 B2
(45) Date of Patent: Dec. 5, 2023

(54) METHODS FOR QUANTIFYING LIGAND EFFICACY IN G-PROTEIN COUPLED RECEPTORS USING SINGLE-MOLECULE FLUORESCENCE ENERGY TRANSFER

(71) Applicant: Cornell University, Ithaca, NY (US)

(72) Inventors: Scott C. Blanchard, Ithaca, NY (US); Gabriel Glenn Gregorio, Ithaca, NY (US); Brian Kobilka, Ithaca, NY (US)

(73) Assignees: CORNELL UNIVERSITY, Ithaca, NY (US); THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 596 days.

(21) Appl. No.: 16/642,181

(22) PCT Filed: Aug. 31, 2018

(86) PCT No.: PCT/US2018/049275
§ 371 (c)(1),
(2) Date: Feb. 26, 2020

(87) PCT Pub. No.: WO2019/046826
PCT Pub. Date: Mar. 7, 2019

(65) Prior Publication Data
US 2021/0072155 A1  Mar. 11, 2021

Related U.S. Application Data

(60) Provisional application No. 62/553,708, filed on Sep. 1, 2017.

(51) Int. Cl.
| | | |
|---|---|---|
| *G01N 21/64* | (2006.01) | |
| *C12Q 1/6818* | (2018.01) | |
| *C07K 14/705* | (2006.01) | |
| *G01N 33/58* | (2006.01) | |
| *G01N 33/94* | (2006.01) | |
| *G01N 33/542* | (2006.01) | |

(52) U.S. Cl.
CPC ... *C07K 14/70571* (2013.01); *G01N 21/6408* (2013.01); *G01N 33/542* (2013.01); *G01N 33/582* (2013.01); *G01N 33/9433* (2013.01); *G01N 2021/6421* (2013.01); *G01N 2333/4719* (2013.01)

(58) Field of Classification Search
CPC ..... C07K 14/70571; G01N 2021/6421; G01N 21/6408; G01N 2333/4719; G01N 33/542; G01N 33/582; G01N 33/68; G01N 33/9433
See application file for complete search history.

(56) References Cited

PUBLICATIONS

Terry P. Kenakin, Chapter 5, "Agonists: The Measurement of Affinity and Efficacy in Functional Assays," In: A Pharmacology Primer. Theory, Applications, and Methods, Third Edition, 2009, pp. 81-82.*
Strange, "Use of the GTPγS ([35S]GTPγS and Eu-GTPγS) binding assay for analysis of ligand potency and efficacy at G protein-coupled receptors," Br. J. Pharmacol., 2010, vol. 161, No. 6, pp. 1238-1249.*
Tetens et al., "Potency of Adrenaline and Noradrenaline for β-Adrenergic Proton Extrusion From Red Cells of Rainbow Trout, Salmo Gairdneri," J. Exp. Biol., 1988, vol. 134, No. 1, pp. 267-280.*
Murakoshi et al., "Single-molecule imaging analysis of Ras activation in living cells," PNAS, 2004, vol. 101, No. 19, pp. 7317-7322.*
Veya et al., "Single Molecule Imaging Deciphers the Relation between Mobility and Signaling of a Prototypical G Protein-coupled Receptor in Living Cells," J. Biol. Chem., 2015, vol. 290, No. 46, pp. 27723-27735.*
International Preliminary Report on Patentability on PCT PCT/US2018/049275 dated Mar. 12, 2020.
Gregorio, et al., "Single-molecule analysis of ligand efficacy in beta2AR-G Protein Activation," Nature, vol. 547(7661), pp. 68-73 (Jul. 2017).
Yao, et al., "The Effect of Ligand Efficacy on the Formation and Stability of a GPCR-G Protein Complex," PNAS, vol. 106(23), pp. 9501-9506 (2009).
Vilardaga, "Studying Ligand Efficacy and G Protein-Coupled Receptors Using FRET," Methods Mol. Biol., vol. 756, pp. 133-148 (2011).
Onaran et al., "Ligand Efficacy and Affinity in an Interacting 7TM Receptor Model," TiPS, vol. 20, pp. 274-278 (1999).
International Search Report and Written Opinion issued in International Patent Application No. PCT/US2018/49275, dated Nov. 15, 2018.

* cited by examiner

*Primary Examiner* — Galina M. Yakovleva
(74) *Attorney, Agent, or Firm* — FOLEY & LARDNER LLP

(57) ABSTRACT

Disclosed herein are methods for providing a molecular efficacy of a ligand, especially when utilizing single-molecule fluorescence resonance energy transfer ("smFRET") imaging, as well as compounds useful in such methods.

16 Claims, 8 Drawing Sheets

METHODS FOR QUANTIFYING LIGAND EFFICACY IN G-PROTEIN COUPLED RECEPTORS USING SINGLE-MOLECULE FLUORESCENCE ENERGY TRANSFER

CROSS-REFERENCE TO RELATED APPLICATIONS

This application is a U.S. National Phase Application under 35 U.S.C. § 371 of International Application No. PCT/US2018/049275, filed on Aug. 31, 2018, which claims the benefit of priority to U.S. Provisional Patent Application No. 62/553,708, filed on Sep. 1, 2017, the entire disclosures of which are herein incorporated by reference for any and all purposes.

U.S. GOVERNMENT RIGHTS

This invention was made with government support under Grant Nos. DA035485, GM083118, and NS028471 awarded by the National Institutes of Health. The government has certain rights in the invention.

SUMMARY

Disclosed herein are methods for providing a molecular efficacy of a ligand, especially when utilizing single-molecule fluorescence resonance energy transfer ("smFRET") imaging, as well as compounds useful in such methods.

In an aspect, the present technology provides a method for providing a molecular efficacy of a ligand. The method includes normalizing an effective rate of generating $G_s(GTP)$ from $G_s(GDP)$ provided by the ligand to an effective rate of adrenaline in generating $G_s(GTP)$ from $G_s(GDP)$ to provide a normalized value $\eta_1$; and normalizing an apparent $EC_{50}$ for GDP binding of the ligand to an apparent $EC_{50}$ for GDP binding of adrenaline to provide a normalized value $\eta_2$; where a value greater than 1.0 for the product of $\eta_1$ and $\eta_2$ ($\eta_1$ multiplied by $\eta_2$) indicates the ligand is more efficacious than adrenaline.

In a related aspect, the present technology provides a method for providing a molecular efficacy of a ligand where the method includes detecting an effective rate of generating $G_s(GTP)$ from $G_s(GDP)$ provided by the ligand ("ligand effective rate"); and detecting an apparent $EC_{50}$ for GDP binding of the ligand ("ligand $EC_{50}$"); where a value greater than 1.0 for the product of $\eta_1$ and $\eta_2$ indicates the ligand is more efficacious than adrenaline, where $\eta_1$ is the ligand effective rate normalized to an effective rate of adrenaline in generating $G_s(GTP)$ from $G_s(GDP)$; and $\eta_2$ is the ligand $EC_{50}$ normalized to an apparent $EC_{50}$ for GDP binding of adrenaline.

In any aspect or embodiment of the methods disclosed herein, the method may include a $\beta_2AR$ labelled with a compound as depicted in the formula below

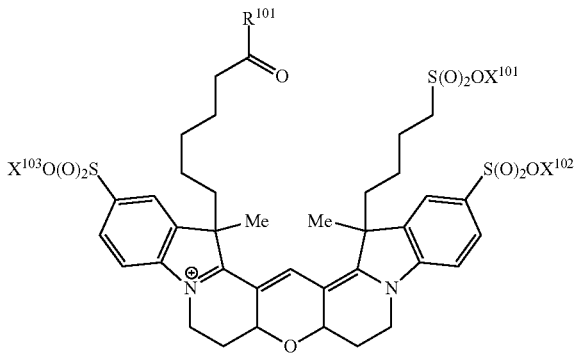

(referred to alternatively hereafter as "Cy3B*-labelled $\beta_2AR$"), where $R^{101}$ is $O-R^{102}$, $O-(C_1-C_6$ alkylene$)-R^{102}$, $NH-R^{102}$, $NH-(C_1-C_{12}$ alkylene$)-NH-R^{102}$, or $NH-(C_1-C_{12}$ alkylene$)-NH-C(O)(CH_2)_o-R^{102}$; o is 1, 2, 3, 4, 5, or 6; $R^{102}$ is a residue of the $\beta_2AR$; and $X^{101}$, $X^{102}$, and $X^{103}$ are each independently H or a lone pair of electrons (i.e. providing an oxygen anion).

In any aspect or embodiment of the methods disclosed herein, the method may alternatively or additionally include a $\beta_2AR$ labelled with a compound as depicted in the formula below

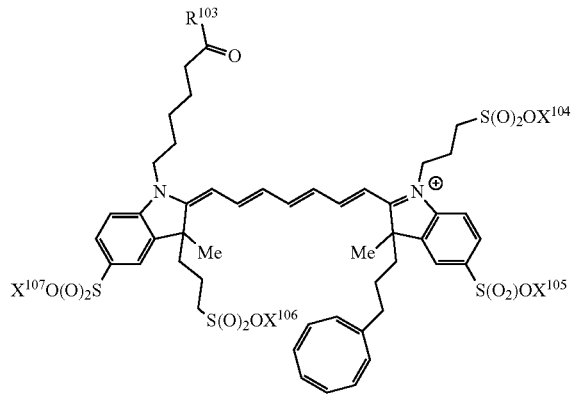

(referred to alternatively hereafter as "Cy7*-labelled $\beta_2AR$"), where $R^{103}$ is $O-R^{104}$, $O-(C_1-C_6$ alkylene$)-R^{104}$, $NH-R^{104}$, $NH-(C_1-C_{12}$ alkylene$)-NH-R^{104}$, or $NH-(C_1-C_{12}$ alkylene$)-NH-C(O)(CH_2)_o-R^{104}$; p is 1, 2, 3, 4, 5, or 6; $R^{104}$ is a residue of the $\beta_2AR$; and $X^{104}$, $X^{105}$, $X^{106}$, and $X^{107}$ are each independently H or a lone pair of electrons (i.e. providing an oxygen anion).

In a related aspect, a compound useful in smFRET imaging is provided, wherein the compound is

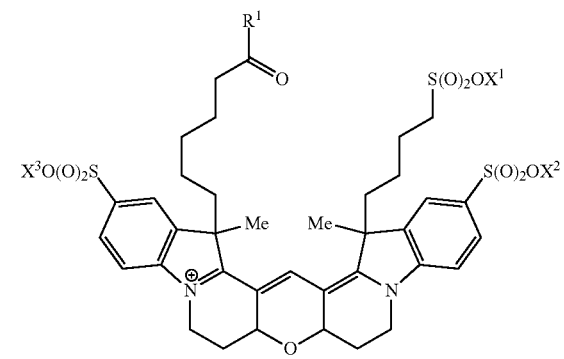

or a pharmaceutically acceptable salt and/or solvate thereof, where $R^1$ is OH, O⁻, O—($C_1$-$C_6$ alkyl), $NH_2$, NH—($C_1$-$C_{12}$ alkylene)-$NH_2$, or NH—($C_1$-$C_{12}$ alkylene)-NH—C(O)($CH_2$)$_n$—$R^2$; n is 1, 2, 3, 4, 5, or 6; $R^2$ is Cl, Br, or I; and $X^1$, $X^2$, and $X^3$ are each independently H or a lone pair of electrons (i.e. providing an oxygen anion).

In a further related aspect, the present technology provides a different compound useful in smFRET imaging, where the compound is

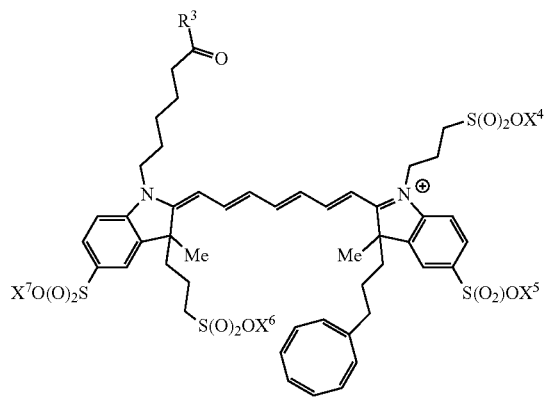

or a pharmaceutically acceptable salt and/or solvate thereof, wherein $R^3$ is OH, O⁻, O—($C_1$-$C_6$ alkyl), $NH_2$, NH—($C_1$-$C_{12}$ alkylene)-$NH_2$, or NH—($C_1$-$C_{12}$ alkylene)-NH—C(O)($CH_2$)$_m$—$R^4$; m is 1, 2, 3, 4, 5, or 6; $R^4$ is Cl, Br, or I; and $X^4$, $X^5$, $X^6$, and $X^7$ are each independently H or a lone pair of electrons (i.e. providing an oxygen anion).

DETAILED DESCRIPTION

Figure 1:
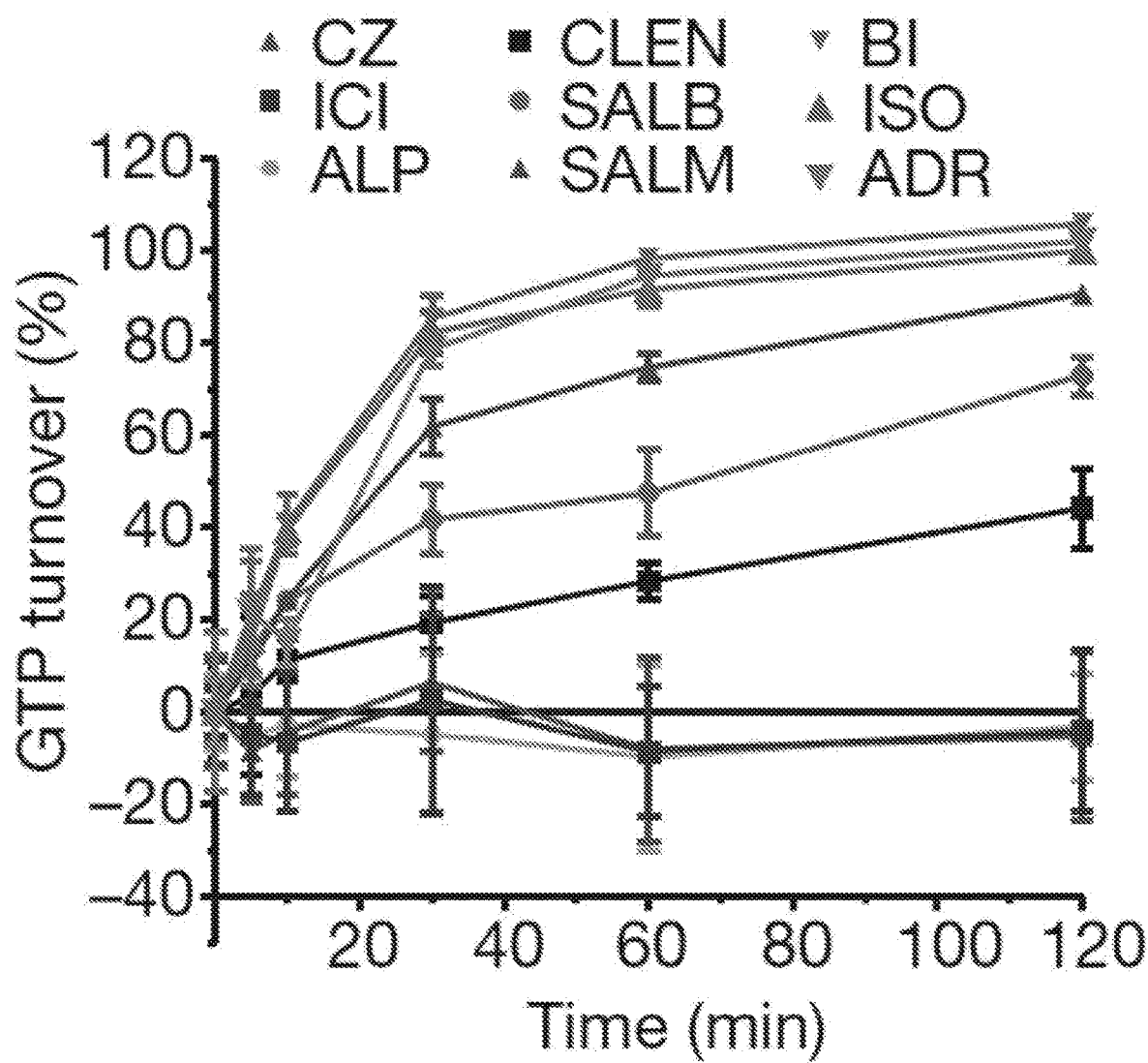
FIG. 1 provides ligand efficacy profiles in terms of GTP turnover for adrenaline (ADR); alprenolol (ALP); BI-167107 (BI); clenbuterol (CLEN); carazolol (CZ); isoproterenol (ISO); salbuterol (SALB); salmeterol (SAM), as discussed in the working examples regarding the present technology.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" and "approximately" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term (e.g., "about 10% by weight"=about 9% by weight to about 11% by weight) and "approximately" will mean up to plus or minus 10% of the particular term (e.g., "about 10% by volume"=about 9% by volume to about 11% by volume).

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

As used herein, $C_m$-$C_n$, such as $C_1$-$C_{12}$, $C_1$-$C_8$, or $C_1$-$C_6$ when used before a group refers to that group containing m to n carbon atoms.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups.

Groups described herein having two or more points of attachment (i.e., divalent, trivalent, or polyvalent) within the compound of the present technology are designated by use of the suffix, "ene." For example, divalent alkyl groups are alkylene groups. Groups having a single point of attachment to the compound of the present technology are not referred to using the "ene" designation. Thus, e.g., chloroethyl is not referred to herein as chloroethylene.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

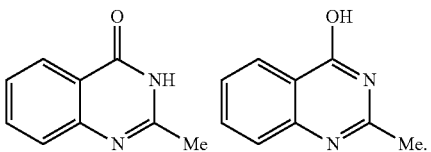

As another example, guanidines may exhibit the following isomeric forms in protic organic solution, also referred to as tautomers of each other:

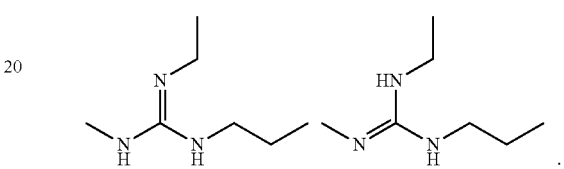

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Throughout this disclosure, various publications, patents and published patent specifications are referenced by an identifying citation. Also within this disclosure are Arabic numerals referring to referenced citations, the full bibliographic details of which are provided subsequent to the Examples section. The disclosures of these publications, patents and published patent specifications are hereby incorporated by reference into the present disclosure to more fully describe the present technology. Further, the article Gregorio, G. G., et al. "Single-molecule analysis of ligand efficacy in β$_2$AR-G-protein activation" *Nature* 547, 68-73 (6 Jul. 2017) doi: 10.1038/nature22354 is incorporated herein by reference for any and all purposes.

The Present Technology

GPCRs regulate cellular responses to neurotransmitters and hormones and act as ligand-regulated guanosine nucleotide exchange factors (GEFs) for heterotrimeric G proteins[1]. Ligand efficacy has historically referred to the capacity of a molecule to elicit a specific physiological response downstream of receptor activation[2,3]. Although an important parameter in drug development, the molecular basis of efficacy with respect to the effect of a ligand on GPCR structure, dynamics and G protein coupling remains poorly understood.

$\beta_2AR$, a paradigmatic, class A GPCR, couples preferentially to the heterotrimeric $G_s$ protein, consisting of $G\alpha_s$, $G\beta$ and $G\gamma$[4]. Investigations of the $\beta_2AR$ activation mechanism have been enabled by synthetic ligands with efficacy profiles ranging from inverse agonists that suppress basal activity, and neutral antagonists that prevent agonist-induced activation, to partial and full agonists that differentially promote receptor-mediated $G_s$ activation[5]. Recent crystallographic structures of distinct class A GPCRs in both inactive and active states[6-9] revealed that the largest conformational change associated with their activation is an outward movement of the cytoplasmic end of TM6[6]. In the nucleotide-free $\beta_2AR$-$G_s$ complex, TM6 is stabilized in an outward configuration by insertion of the C-terminal α 5 helix of $G\alpha_s$ into a pocket formed by the cytoplasmic ends of TM3, TM5 and TM6 and intracellular loop 2 (ICL2).

Ensemble techniques, including fluorescence[10], electron paramagnetic resonance (EPR)[11] and nuclear magnetic resonance (NMR) spectroscopy[11,12] reveal that even the most potent agonists fail to fully stabilize $\beta_2AR$ in its activated conformation in the absence of G protein or stabilizing nanobodies.

The present technology is based on the inventors' insight that the molecular basis of ligand efficacy may be defined by changes in receptor dynamics and conformation that impact the probability of G-protein coupling, productive nucleotide exchange, and subsequent dissociation. The inventors utilized single-molecule fluorescence resonance energy transfer (smFRET) imaging to track TM6 movements in $\beta_2AR$ bound to ligands with distinct efficacy profiles to determine the effects on receptor structure, dynamics, and G-protein coupling, and via such insight and studies conceived of the methods and compounds of the present technology.

Thus, in an aspect, the present technology provides a method for providing a molecular efficacy of a ligand. The method includes normalizing an effective rate of generating $G_s(GTP)$ from $G_s(GDP)$ provided by the ligand to an effective rate of adrenaline in generating $G_s(GTP)$ from $G_s(GDP)$ to provide a normalized value $\eta_1$; and normalizing an apparent $EC_{50}$ for GDP binding of the ligand to an apparent $EC_{50}$ for GDP binding of adrenaline to provide a normalized value $\eta_2$; where a value greater than 1.0 for the product of $\eta_1$ and $\eta_2$ ($\eta_1$ multiplied by $\eta_2$) indicates the ligand is more efficacious than adrenaline. The method may further include smFRET imaging of a complex of $G_s$ with Cy3B*/Cy7*-labelled $\beta_2\Delta6$-N148C/L266C in the presence of a saturating concentration of the ligand, a concentration of $G_s$, and a concentration of apyrase. The method of any embodiment herein may further include smFRET of Cy3B*/Cy7*-labelled $\beta_2\Delta6$-N148C/L266C in the presence of a saturating concentration of the ligand, a concentration of GDP, and two or more different concentrations of $G_s$; wherein at least two of the two or more different concentrations of $G_s$ are each below a saturating concentration of $G_s$. Such smFRET imaging may precede the normalizing steps.

In a related aspect, the present technology provides a method for providing a molecular efficacy of a ligand where the method includes detecting an effective rate of generating $G_s(GTP)$ from $G_s(GDP)$ provided by the ligand ("ligand effective rate"); and detecting an apparent $EC_{50}$ for GDP binding of the ligand ("ligand $EC_{50}$"); where a value greater than 1.0 for the product of $\eta_1$ and $\eta_2$ indicates the ligand is more efficacious than adrenaline, where $\eta_1$ is the ligand effective rate normalized to an effective rate of adrenaline in generating $G_s(GTP)$ from $G_s(GDP)$; and $\eta_2$ is the ligand $EC_{50}$ normalized to an apparent $EC_{50}$ for GDP binding of adrenaline. Detecting the ligand effective rate may include smFRET imaging. Detecting the apparent $EC_{50}$ for GDP binding of the ligand may include smFRET imaging. The method may further include detecting the effective rate of adrenaline in generating $G_s(GTP)$ from $G_s(GDP)$, optionally where such detecting includes smFRET imaging. In any aspect or embodiment disclosed herein, the method may further include detecting the apparent $EC_{50}$ for GDP binding of adrenaline, where such detecting includes smFRET imaging.

In any aspect or embodiment of the methods disclosed herein, the method may include a $\beta_2AR$ labelled with a compound as depicted in the formula below

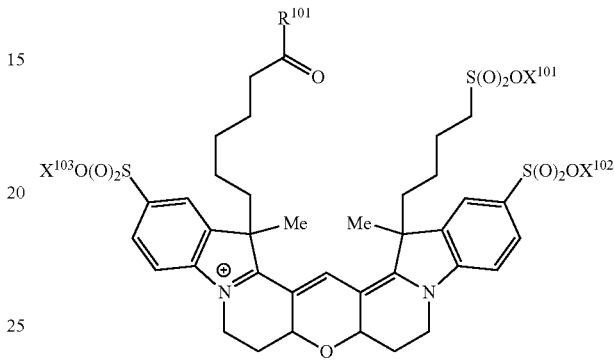

(referred to alternatively hereafter as "Cy3B*-labelled $\beta_2AR$"), where $R^{101}$ is O—$R^{102}$, O—($C_1$-$C_6$ alkylene)-$R^{102}$, NH—$R^{102}$, NH—($C_1$-$C_{12}$ alkylene)-NH—$R^{102}$, or NH—($C_1$-$C_{12}$ alkylene)-NH—C(O)($CH_2$)$_o$—$R^{102}$; o is 1, 2, 3, 4, 5, or 6; $R^{102}$ is a residue of the $\beta_2AR$; and $X^{101}$, $X^{102}$, and $X^{103}$ are each independently H or a lone pair of electrons (i.e. providing an oxygen anion). The $\beta_2AR$ may be a mutant of native $\beta_2AR$, such as a mutant of native $\beta_2AR$ that includes replacing an amino acid of native $\beta_2AR$ with a cysteine (e.g., a mutant of native $\beta_2AR$ that comprises replacing N148 of native $\beta_2AR$ with a cysteine and/or a mutant of native $\beta_2AR$ that comprises replacing L266 of native $\beta_2AR$ with a cysteine). In any aspect or embodiment herein, $R^{102}$ may be S of a cysteine residue side chain of the $\beta_2AR$ (of any embodiment disclosed herein).

In any aspect or embodiment of the methods disclosed herein, the method may alternatively or additionally include a $\beta_2AR$ labelled with a compound as depicted in the formula below

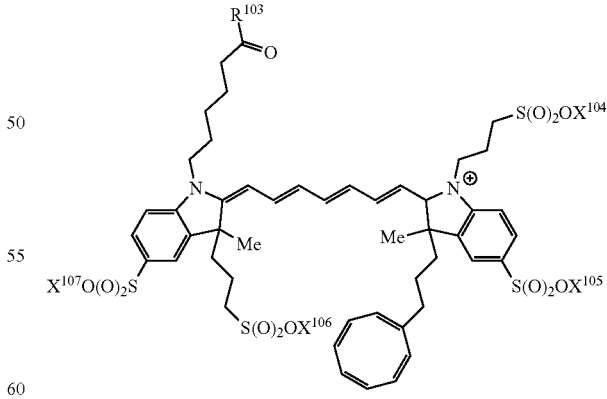

(referred to alternatively hereafter as "Cy7*-labelled $\beta_2AR$"), where $R^{103}$ is O—$R^{104}$, O—($C_1$-$C_6$ alkylene)-$R^{104}$, NH—$R^{104}$, NH—($C_1$-$C_{12}$ alkylene)-NH—$R^{104}$, or NH—($C_1$-$C_{12}$ alkylene)-NH—C(O)($CH_2$)$_o$—$R^{104}$; p is 1, 2, 3, 4, 5, or 6; $R^{104}$ is a residue of the $\beta_2AR$; and $X^{104}$, $X^{105}$, $X^{106}$, and $X^{107}$ are each independently H or a lone pair of electrons (i.e. providing an oxygen anion). The $\beta_2AR$ may be a mutant of native β$_2$AR, such as a mutant of native β$_2$AR that includes replacing an amino acid of native β$_2$AR with a cysteine (e.g., a mutant of native β$_2$AR that comprises replacing N148 of native β$_2$AR with a cysteine and/or a mutant of native β$_2$AR that comprises replacing L266 of native β$_2$AR with a cysteine). In any aspect or embodiment herein, R$^{104}$ may be S of a cysteine residue side chain of the β$_2$AR (of any embodiment disclosed herein).

In any aspect or embodiment disclosed herein, the method may include a β$_2$AR that is both Cy3B*-labelled and Cy7*-labelled ("Cy3B*/Cy7*-labelled β$_2$AR"). For example, the method may include smFRET imaging of a complex of G$_s$ with Cy3B*/Cy7*-labelled β$_2$AR in the presence of a saturating concentration of the ligand, a concentration of G$_s$, and a concentration of apyrase; and/or the method may include smFRET of Cy3B*/Cy7*-labelled β$_2$AR in the presence of a saturating concentration of the ligand, a concentration of GDP, and two or more different concentrations of G$_s$; wherein at least two of the two or more different concentrations of G$_s$ are each below a saturating concentration of G$_s$.

In a related aspect, a compound useful in smFRET imaging is provided, wherein the compound is

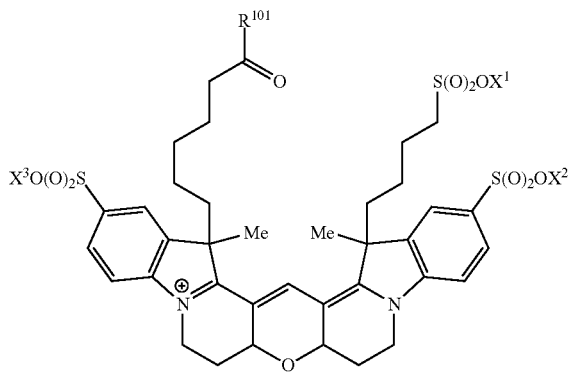

or a pharmaceutically acceptable salt and/or solvate thereof, where R$^1$ is OH, O$^-$, O—(C$_1$-C$_6$ alkyl), NH$_2$, NH—(C$_1$-C$_{12}$ alkylene)-NH$_2$, or NH—(C$_1$-C$_{12}$ alkylene)-NH—C(O)(CH$_2$)$_n$—R$^2$; n is 1, 2, 3, 4, 5, or 6; R$^2$ is Cl, Br, or I; and X$^1$, X$^2$, and X$^3$ are each independently H or a lone pair of electrons (i.e. providing an oxygen anion).

In a further related aspect, the present technology provides a different compound useful in smFRET imaging, where the compound is

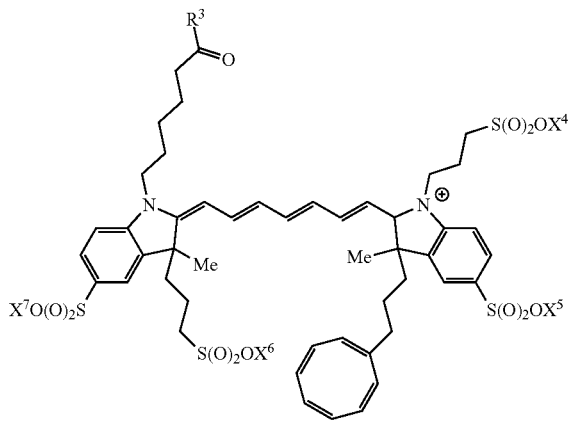

or a pharmaceutically acceptable salt and/or solvate thereof, wherein R$^3$ is OH, O$^-$, O—(C$_1$-C$_6$ alkyl), NH$_2$, NH—(C$_1$-C$_{12}$ alkylene)-NH$_2$, or NH—(C$_1$-C$_{12}$ alkylene)-NH—C(O)(CH$_2$)$_m$—R$^4$; m is 1, 2, 3, 4, 5, or 6; R$^4$ is Cl, Br, or I; and X$^4$, X$^5$, X$^6$, and X$^7$ are each independently H or a lone pair of electrons (i.e. providing an oxygen anion).

The examples herein are provided to illustrate advantages of the present technology and to further assist a person of ordinary skill in the art with preparing or using the present technology. The examples herein are also presented in order to more fully illustrate the preferred aspects of the present technology. The examples should in no way be construed as limiting the scope of the present technology. The examples can include or incorporate any of the variations, aspects, or embodiments of the present technology described above. The variations, aspects, or embodiments described above may also further each include or incorporate the variations of any or all other variations, aspects, or embodiments of the present technology.

EXAMPLES

Fluorophore synthesis. Specialized cyanine fluorophores, Cy3B* and Cy7*, utilized were synthesized following established procedures for Cy3™ and Cy7™ synthesis from sulfonated indole cyanine constituents[36] (U.S. Pat. Nos. 8,945,515, 6,133,445, Int'l Pat. Appl. No. PCT/US2013/022107) with the following specific modifications. Cy3B* was synthesized from indole precursors to orient the linker moiety for protein coupling to the methyl substituent of the indole ring. The negative charge density for each indole was maximized by sulfonation of the benzene ring as well as its methyl substituent. The resulting Cy3B* carboxylic acid was converted to an N-hydroxysuccinimide (NHS) ester using standard protocols. The starting material for the Cy7* fluorophore in which the cycloocta-1,3,5,7-tetraene (cyclooctatetraene) moiety is oriented opposite to the linker moiety for protein coupling (LD750-NHS) was obtained from Lumidyne Technologies. To extend the distance between both Cy3B* and Cy7* fluorophores and β$_2$AR, the six-atom, NHS-activated linker extending from the indole nitrogen atom was coupled to pentane-1,5-diamine (cadaverine), which was subsequently activated with iodoacetamide to enable cysteine reactivity (referred to respectively herein as "activated Cy3B*" and "activated Cy7*").

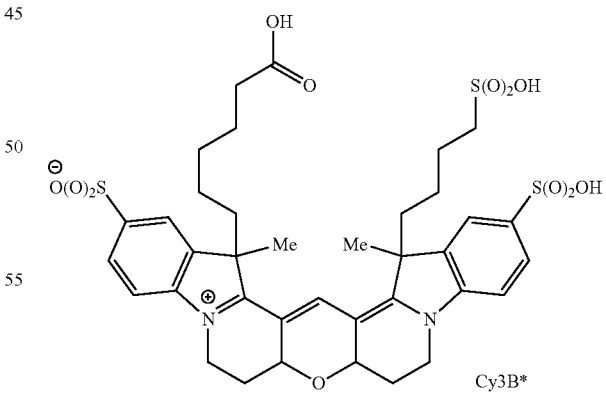

Cy3B*: $^1$H NMR (500 MHz, MeOD-d4): δ 8.24 p.p.m. (d, 1H, J=21.7 Hz), 7.95 (m, 4H), 7.37 (m, 2H), 4.83 (dd, 1H, J1=11.3 Hz, J2=5.0 Hz), 4.70 (m, 1H), 4.44 (m, 1H), 4.01-3.94 (m, 2H), 2.65 (m, 4H), 2.23 (m, 2H), 1.94 (s, 2H), 1.83 (d, J=10 Hz, 3H), 1.79 (s, 3H), 1.63 (m, 2H), 1.50 (m, 2H), 1.25-0.78 (m, 6H).

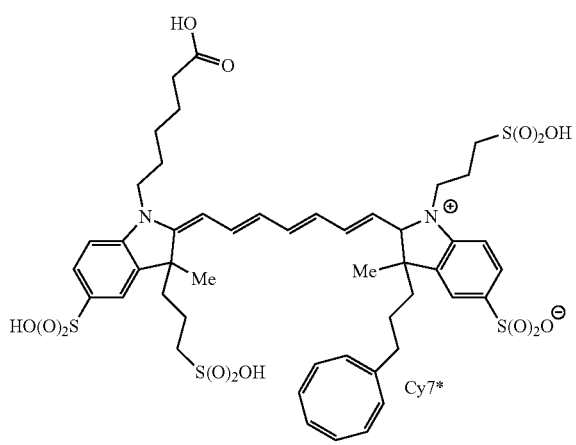

Cy7*: ¹H NMR (500 MHz, MeOD-d4): δ 8.00 p.p.m. (m, 2H), 7.90 (m, 4H), 7.84 (s, 1H), 7.42 (d, 1H, J=8.3 Hz), 7.35 (d, 1H, J=8.3 Hz), 6.68 (m, 2H), 6.54 (d, 1H, J=13.5 Hz), 6.43 (d, 1H, J=13.5 Hz), 5.79-5.70 (b, 5H), 5.48 (m, 2H), 4.33 (t, 2H, J=7.2 Hz), 4.13 (t, 2H, J=7.2 Hz), 3.00 (t, 2H, J=6.7 Hz), 2.64 (m, 2H), 2.40 (m, 2H), 2.30-2.23 (m, 8H), 1.94 (s, 2H), 1.84 (m, 2H), 1.75 (s, 3H), 1.73 (s, 3H), 1.70-1.68 (m, 2H), 1.54 (m, 2H), 1.05 (b, 2H), 0.72 (b, 2H).

Exemplary detailed description of Cy3B* synthesis. In a round bottom flask, 5 ml of 38% hydrobromic acid (HBr) in water was added to the potassium salt of indole 1 (440 mg) and the reaction mixture was stirred at room temperature for 1 h and then vacuum dried. The dried material was dissolved in 3 ml of tetrahydrothiophene 1,1-dioxide (sulfolane), followed by the addition of 500 μl acrolein diethyl acetal. This reaction solution was heated to 70° C. for 40 min, cooled to room temperature and precipitated by the addition of 40 ml ethyl acetate (EtOAc). The desired product, compound 2 (403 mg), was recovered as a purple solid (recovery yield 82%) and carried onto the next step without further purification. ESI-MS (m/z): [M-H]⁻ calculated for C21H34NO8S2, 491.2; found, 491.1.

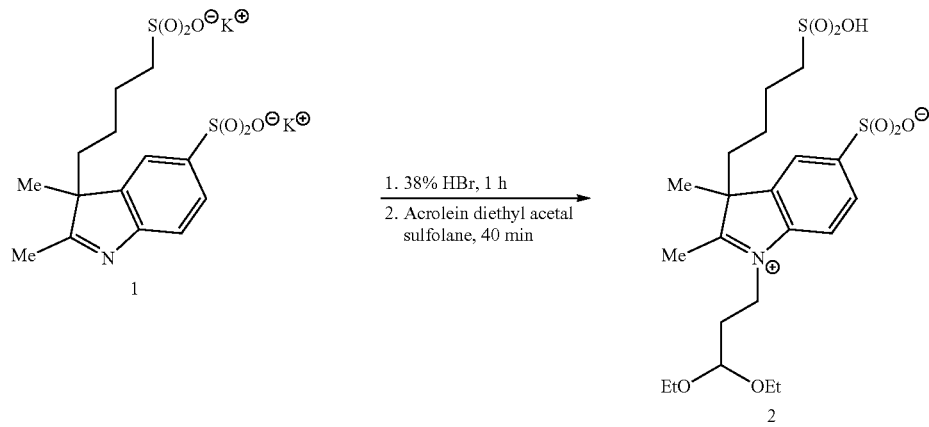

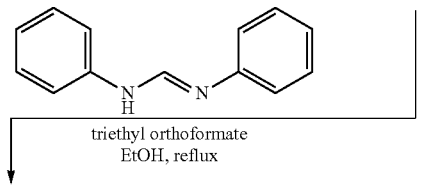

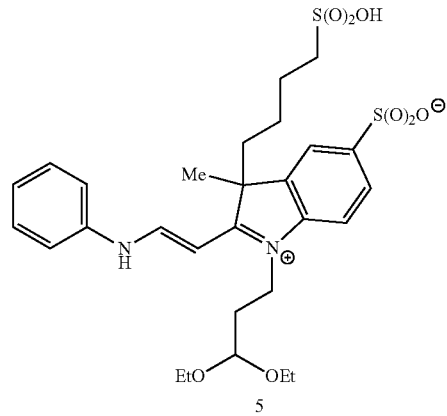

In a round bottom flask, compound 2 (169 mg) was dissolved in 10 ml ethanol. 135 mg N,N'-diphenylformamidine and 0.11 ml triethyl orthoformate were then added to this solution. The reaction mixture was refluxed for 24 h, then poured into 40 ml of 1:1 hexane:EtOAc. The precipitate was collected and purified by reversed phase C18 column with 0.1% formic acid solution using an acetonitrile solvent gradient. The desired product 5 (148 mg), was recovered as a purple solid (recovery yield 58.9%) and carried onto the next step without further purification. ESI-MS (m/z): [M-H]⁻ calculated for C28H38N2O8S2, 593.2; found, 593.2.

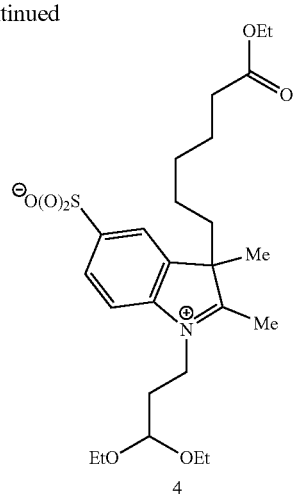

4

In a round bottom flask, 5 ml of 38% HBr in water and 3 ml ethanol was mixed with the potassium salt of indole 3 (208 mg) and the reaction mixture was stirred at room temperature for 1 h and then vacuum dried. The dried material was dissolved in 2 ml of acetonitrile and 200 μl acrolein diethyl acetal. The reaction solution was heated to 70° C. for 40 min, cooled to room temperature and then vacuum dried to remove solvent. The dried material was silica gel purified using 20% MeOH in dichloromethane (DCM) as the mobile phase. The desired product 4 was then further purified by reversed phase C18 column equilibrated with 0.1% formic acid solution using an acetonitrile solvent gradient. Pure product 4 (68.2 mg) was obtained as a purple solid (yield 27.3%) and carried onto the next step without further purification. ESI-MS (m/z): [M-H]⁻ calculated for C23H36NO7S, 469.2; found, 469.3.

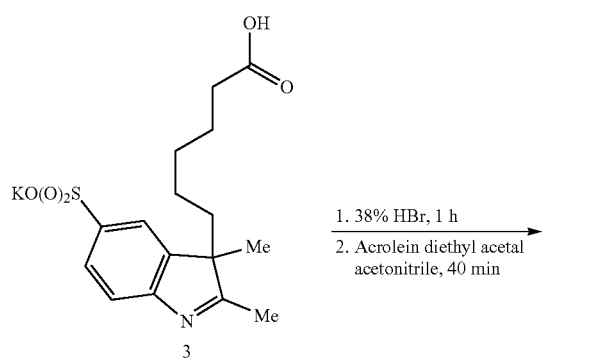

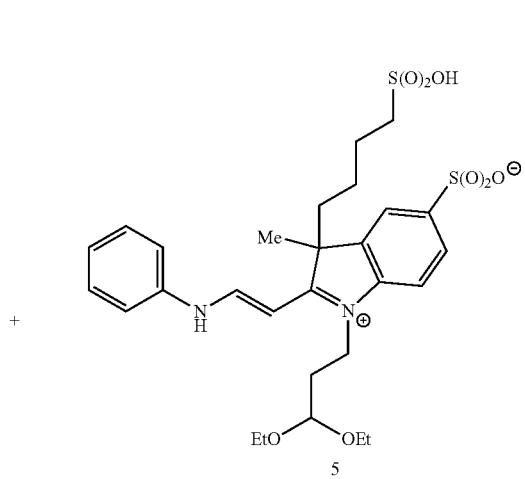

Pyridine, acetic anhydride
100° C., 3 h

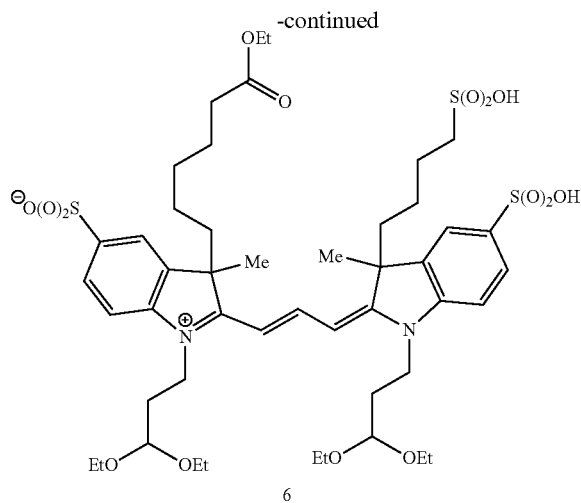

6

In a round bottom flask, compound 5 (59 mg), compound 4 (50 mg), pyridine (3 ml) and acetic anhydride (150 μl) were added. The reaction solution was heated to 100° C. for 3 h, then poured into 40 ml EtOAC. The precipitate was purified by reversed phase C18 column with 0.1% formic acid solution using an acetonitrile solvent gradient. Pure product 6 (53 mg) was obtained as a red solid (recovery yield 53.1%). ESI-MS (m/z): [M-H]$^-$ calculated for C46H68N2O15S3, 997.4; found, 997.4.

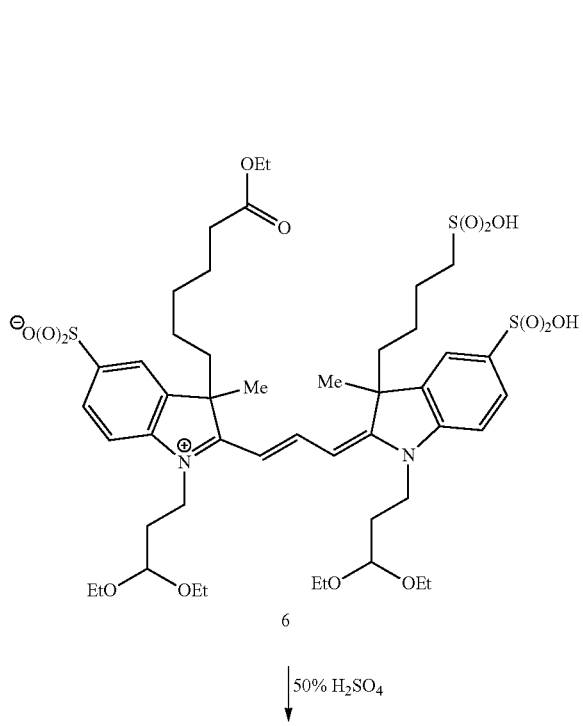

6

↓ 50% H$_2$SO$_4$

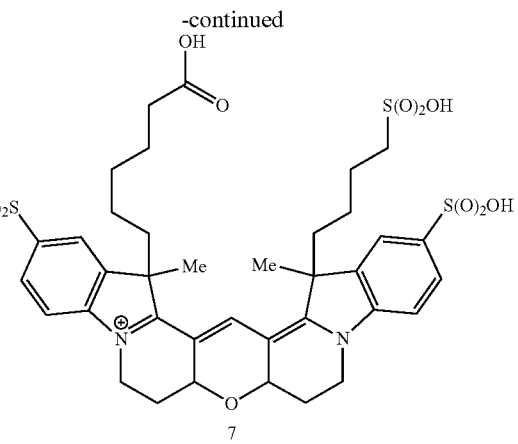

7

In a round bottom flask, 53 mg of compound 6 was dissolved in 6 ml of 50% sulfuric acid. The bright red solution was stirred at room temperature in the dark for 2 h. The reaction solution was then diluted with 200 ml water, loaded onto a Sep-Pak cartridge and eluted with 95% acetonitrile. The resulting solution was vacuum dried and purified by reversed phase C18 column with 0.1% formic acid solution using an acetonitrile solvent gradient. Pure Cy3B* product 7 (16 mg) was obtained as a red solid (recovery yield 37.2%). ESI-MS (m/z): [M-H]$^-$ calculated for C37H44N2O12S3, 803.2; found, 803.1.

Schematic of fluorophore activation:

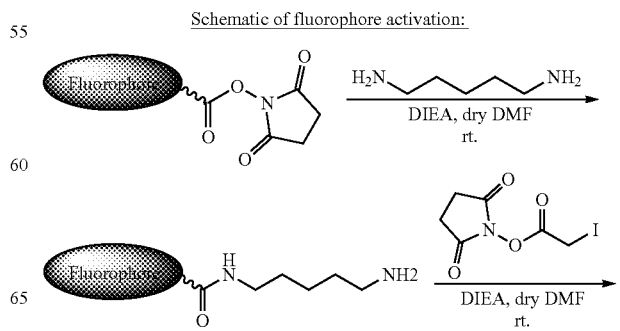

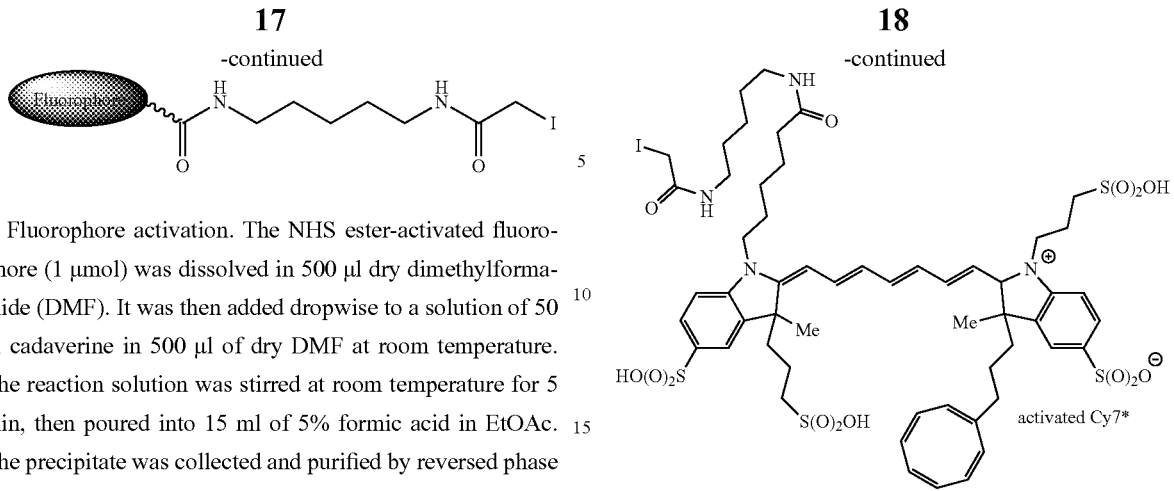

Fluorophore activation. The NHS ester-activated fluorophore (1 μmol) was dissolved in 500 μl dry dimethylformamide (DMF). It was then added dropwise to a solution of 50 μl cadaverine in 500 μl of dry DMF at room temperature. The reaction solution was stirred at room temperature for 5 min, then poured into 15 ml of 5% formic acid in EtOAc. The precipitate was collected and purified by reversed phase C18 column using 10 mM triethylammonium acetate (TEAA), pH 7.0, aqueous buffer (solvent A) with 100% acetonitrile (solvent B) as the mobile phase. The product fraction was dried using a rotary evaporator. The resulting pure fluorophore-cadaverine compound was then dissolved in 1 ml dry DMF. N,N-diisopropylethylamine (DIEA; 100 μl) was added to this solution, followed by 1 mg iodoacetic acid NHS ester. The reaction solution was stirred at room temperature for 15 min and then poured into 15 ml EtOAc. The precipitate was collected and purified by reversed phase C18 column using solvent A and solvent B as the mobile phase. The yield was 65% over two steps for Cy3B* (ESI-MS (m/z): [M−H]$^-$ calculated for C44H57IN4O12S3, 1055.2; found, 1055.5) and 73% for Cy7* (ESI-MS (m/z): [M−H]$^-$ calculated for C56H73IN4O14S4, 1279.3; found, 1279.2). Analytical HPLC of activated Cy3B* and activated Cy7* products showed their purity to be >95%, where the structures of the final activated Cy3B* and activated Cy7* products are provided below.

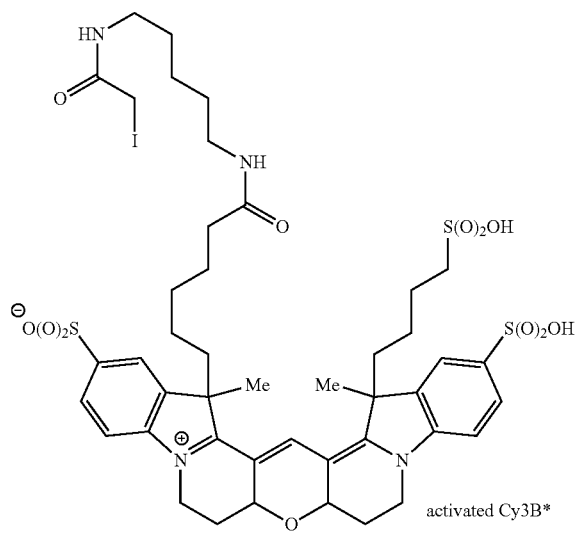

$\beta_2$AR expression, purification and labelling. Mutations N148C and L266C were introduced in a minimal cysteine background ($\beta_2\Delta 6$: C77V, C265A, C327S, C341L, C378A and C406A) of full-length human $\beta_2$AR ($\beta_2\Delta 6$-N148C/L266C) containing an N-terminal FLAG tag and a C-terminal hexahistidine tag. Sf9 insect cells infected with baculovirus encoding the receptor construct were harvested 60 h post-infection and lysed by osmotic shock prior to solubilization of the membrane fraction by n-dodecyl-β-D-maltopyranoside (DDM).

The initial purification step consisted of anti-FLAG antibody chromatography followed by functional purification through alprenolol-sepharose ligand affinity chromatography[6,37]. The purified protein at a concentration of approximately 10 μM was then flash frozen in liquid nitrogen in the presence of 20% glycerol as cryoprotectant. We verified that this procedure preserved a fully functional sample using fluorescence spectroscopy, comparing the activation response on bimane-labelled $\beta_2$AR[10] before and after flash freezing (data not shown).

C266 and C148 in $\beta_2\Delta 6$-N148C/L266C were labelled sequentially with the donor and acceptor fluorophores, respectively, under conditions designed to minimize off-target labelling that achieved dually labelled protein at about 20% efficiency. Purified protein aliquots were brought to room temperature and 100 μM tris(2-carboxyethyl)phosphine (TCEP) and saturating concentrations of atenolol were added; the former to increase labelling efficiency and the latter, a low-affinity antagonist, to stabilize the receptor during labelling. Iodoacetamide-based Cy3B* and Cy7* dyes (i.e., activated Cy3B* and activated Cy7*) were used. Activated Cy3B* was used at a 10-fold molar excess over $\beta_2$AR and incubated at room temperature for 2 h, followed by the addition of a 50-fold molar excess of activated Cy7* and incubation for 3 more hours. Excess dye and ligand were then removed by gel filtration on a 3 ml G50 desalting column and the eluted protein flash frozen in the presence of 15% glycerol. Individual aliquots were used for imaging and never refrozen.

$G_s$ heterotrimer expression and purification. Heterotrimeric $G_s$ was expressed in High Five™ insect cells using baculoviruses generated by the BestBac method (Expression Systems). Two separate baculoviruses were used, one encoding the human Gαs short splice variant and the other encoding both the Gβ 1 and Gγ2 subunits. The sequence for the Gβ1 subunit contained an aminoterminal hexa histidine-tag (6×His) followed by a rhinovirus 3C protease site to remove the 6×His tag during the multistep purification procedure. High Five™ cells were infected with the baculoviruses at a density of 3×106 cells ml⁻¹ followed by an incubation of 48 h at 27° C. Cells were harvested by centrifugation and lysed in a buffer comprised of 10 mM Tris, pH 7.5, 100 µM magnesium chloride (MgCl2), 5 mM β-mercaptoethanol (βME), 50 µM GDP and protease inhibitors. The membrane fraction was collected by centrifugation and solubilized with a buffer comprised of 20 mM HEPES, pH 7.5, 100 mM sodium chloride (NaCl), 1% sodium cholate, 0.05% DDM, 5 mM MgCl2, 5 mM βME, 5 mM imidazole, 50 µM GDP and protease inhibitors. The solubilization reaction was incubated for 45 min at 4° C. after homogenization with a Dounce homogenizer. After centrifugation, the soluble fraction was incubated in batch with Nichelated sepharose for 1.5 h at 4° C. followed by multiple washes of the resin in batch with solubilization buffer supplemented with 15 mM imidazole. The resin was loaded into a wide-bore glass column and the detergent was gradually exchanged to 0.1% DDM. The protein was eluted in buffer supplemented with 200 mM imidazole and dialyzed overnight in 20 mM HEPES, pH 7.5, 100 mM NaCl, 0.1% DDM, 1 mM MgCl2, 5 mM βME and 50 µM GDP. During dialysis, 3C protease (1:1,000 w/w) was added to the dialysis cassette to cleave off the aminoterminal 6×His tag. The cleaved 6×His tag, uncleaved fractions and 3C protease were removed by incubating the protein in batch with Ni-chelated sepharose resin for 45 min at 4° C. Then the slurry was loaded into a wide-bore glass column and the flow through containing heterotrimeric G protein and excess Gβγ was collected. Lambda protein phosphatase (200 units, NEB), calf intestinal phosphatase (10 units, NEB) and antarctic phosphatase (5 units, NEB) were added together with 1 mM manganese chloride to dephosphorylate the protein. After 1 h incubation on ice, the protein solution was diluted two fold with buffer composed of 20 mM HEPES, pH 7.5, 1 mM MgCl2, 0.02% DDM and 100 µM TCEP to adjust the NaCl concentration to 50 mM. The sample was passed through a 0.22 µm filter and loaded onto a MonoQ 10/100 GL column (GE Healthcare) equilibrated in buffer A (20 mM HEPES, pH 7.5, 50 mM NaCl, 1 mM MgCl2, 0.02% DDM, 100 µM TCEP and 20 µM GDP) to separate the heterotrimer from excess Gβγ subunits. The column was washed with 5 column volumes (CV) of buffer A at 4 ml mini and the G protein heterotrimer was eluted over 7.5 CV with a linear gradient of 0-30% buffer B (buffer A with 1 M NaCl). The main peak containing isoprenylated G protein heterotrimer was collected and the protein was dialyzed into 20 mM HEPES, pH 7.5, 100 mM NaCl, 0.02% DDM, 100 µM TCEP and 50 µM GDP. After concentrating the protein to 250 µM, 20% glycerol was added and the protein (final concentration 200 µM) was flash frozen in liquid nitrogen and stored at −80° C. until use.

Biotinylation of the $G_s$ heterotrimer. In order to selectively biotinylate the N-terminal α-amino groups of the $G_s$ subunits, the purified $G_s$ heterotrimer was loaded onto a 2.5 ml G50 super fine (GE Healthcare) column equilibrated with 20 mM MOPS, pH 6.5, 100 mM NaCl, 1 mM MgCl2, 500 µM TCEP, 100 µM GDP and 0.02% DDM to lower the pH from 7.5 to 6.5. After buffer exchange, two-fold molar excess (50 µM) of EZ-Link™ NHS-PEG4-biotin (Thermo Scientific) was added to $G_s$ (25 µM) and incubated for 2 h at 4° C. The reaction was quenched with 100 mM Tris, pH 7.5, for 30 min at 4° C. and free EZ-Link™ NHS-PEG4-biotin was removed by desalting the protein on a G50 super fine column equilibrated with buffer comprised of 20 mM HEPES, pH 7.5, 100 mM NaCl, 1 mM MgCl$_2$, 0.02% DDM, 100 µM TCEP and 50 M GDP. After elution, the protein was concentrated to 250 µM and 20% glycerol was added. The protein (final concentration of 200 µM) was flash frozen in liquid nitrogen and stored at −80° C. until needed. The efficiency of the biotinylation of the $G_s$ subunits was monitored by streptavidin-induced shift on a SDS-polyacrylamide gel.

GTP turnover assay. Analysis of GTP turnover was performed by using a modified protocol of the GTPase-Glo™ assay[38] (Promega). The reaction was started by mixing purified, unliganded or ligand-bound β$_2$AR and G protein in an assay buffer containing 20 mM HEPES, pH 7.5, 100 mM NaCl, 0.1% DDM, 100 µM TCEP, 10 mM MgCl$_2$, 10 µM GDP and 5 µM GTP. After incubation for a given time (FIG. 1), reconstituted GTPase-Glo™ reagent was added to the sample and incubated for 30 min at room temperature. Luminescence was measured after the addition of detection reagent and incubation for 10 min at room temperature using a SpectraMax Paradigm plate reader. The relative light units (RLU) of all ligands were corrected by the values obtained for unliganded receptor and normalized to the maximum response in the presence of isoproterenol at 120 min incubation time.

Figure 2:
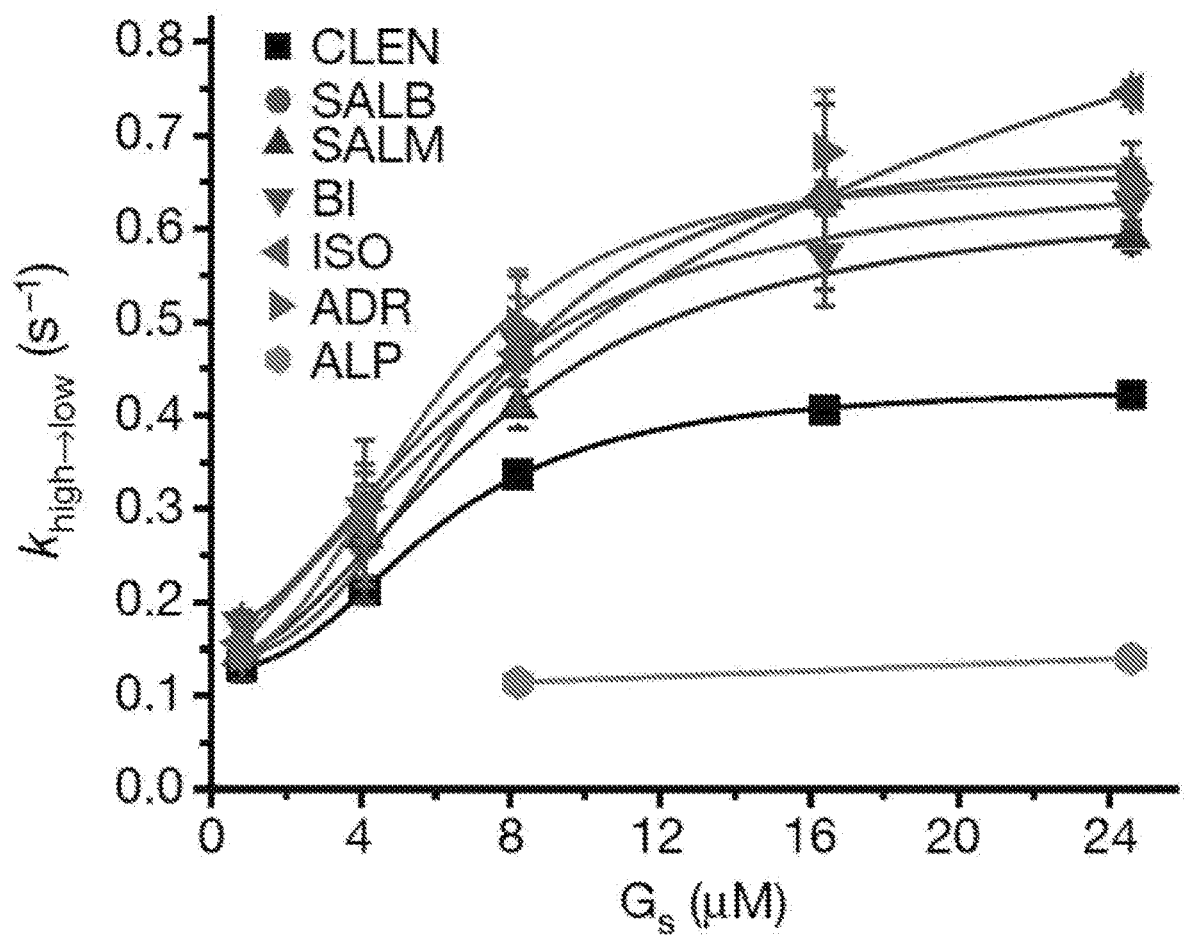
FIG. 2 provides the transition rates from high- to low-FRET states ($k_{high \rightarrow low}$; error bars denote s.d., 2 replicates) with increasing $G_s$(GDP) concentrations for adrenaline (ADR); alprenolol (ALP); BI-167107 (BI); clenbuterol (CLEN); carazolol (CZ); isoproterenol (ISO); salbuterol (SALB); and salmeterol (SAM), as discussed in the working examples regarding the present technology.
Figure 7:
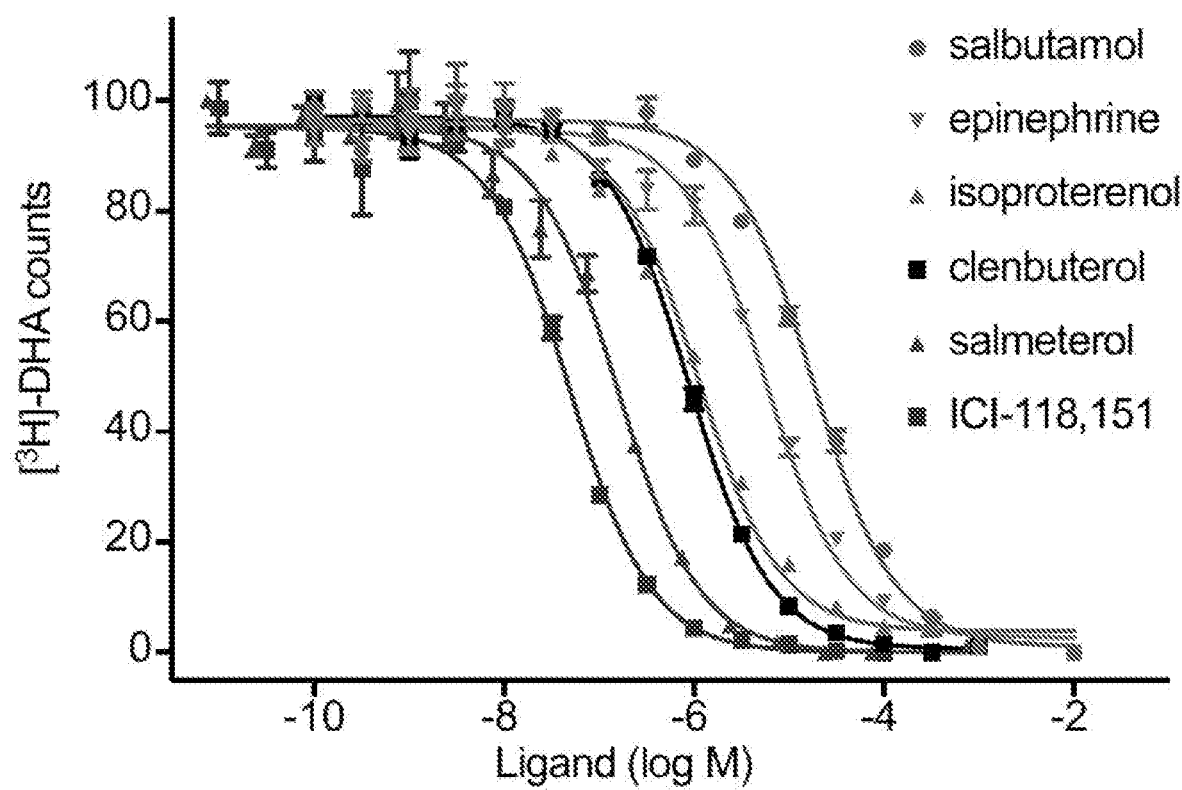
FIG. 7 provides the results of [³H]DHA competition binding on unlabelled $β_2Δ6$-N148C/L266C for ligands used in the working examples, except for carazolol and BI-167107, for which the ultra-high affinities reported (32 pM and 84 pM, respectively) would not allow for accurate determination in the assay; instead, concentrations of 1 µM for both carazolol and BI-167107 were used. The calculated Ki values are provided in Table 4 herein.

Single-molecule FRET experiments. N-terminal FLAG-tagged, Cy3B*/Cy7*-labelled β$_2$Δ6-N148C/L266C (1 nM) was incubated with a saturating concentration of ligand (see Scheme 1, below) (FIG. 7; Table 4) and a substoichiometric amount of biotinylated anti-FLAG antibody M1 Fab fragment for 30 min at room temperature. Complexes were then surface immobilized within polyethylene glycol-passivated, (1,3) trans-divalent streptavidin[39]-coated, quartz microfluidic chambers[40] and imaged in the presence of saturating ligand. For $G_s$ coupling experiments, labelled β$_2$AR was incubated with saturating ligand, biotin-M1-Fab fragment and 8 µM $G_s$ for 30 min at room temperature. Apyrase (0.2 nM) was then added, followed by a 30 min incubation at room temperature to stabilize the nucleotide-free β$_2$AR-$G_s$ complex through the removal of free GDP in solution. Surface-immobilized β$_2$AR-$G_s$ complexes were then imaged in the presence of saturating ligand, 8 µM $G_s$ and 0.2 nM apyrase. For $G_s$ titration experiments, surface-immobilized β$_2$AR was imaged in the presence of saturating ligand, 30 µM GDP and increasing $G_s$ concentrations (0.8-24 µM) (FIG. 2). For nucleotide titration experiments, imaging was performed in the presence of saturating ligand, 8 µM $G_s$ and increasing GDP concentrations (0-100 µM) or increasing GTP concentrations (0-100 µM) in 30 µM GDP. In these experiments, the concentration of immobilized receptor is not sufficient to change significantly the concentrations of free, GDP-bound $G_s$ or nucleotides, during the course of observation.

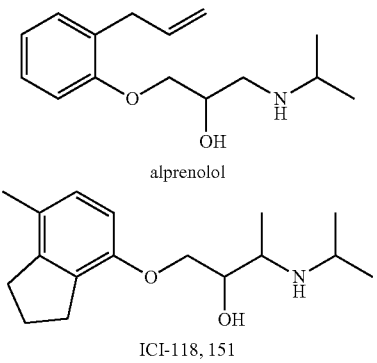

Scheme 1
Structures of ligands used in present Examples alprenolol

ICI-118,151

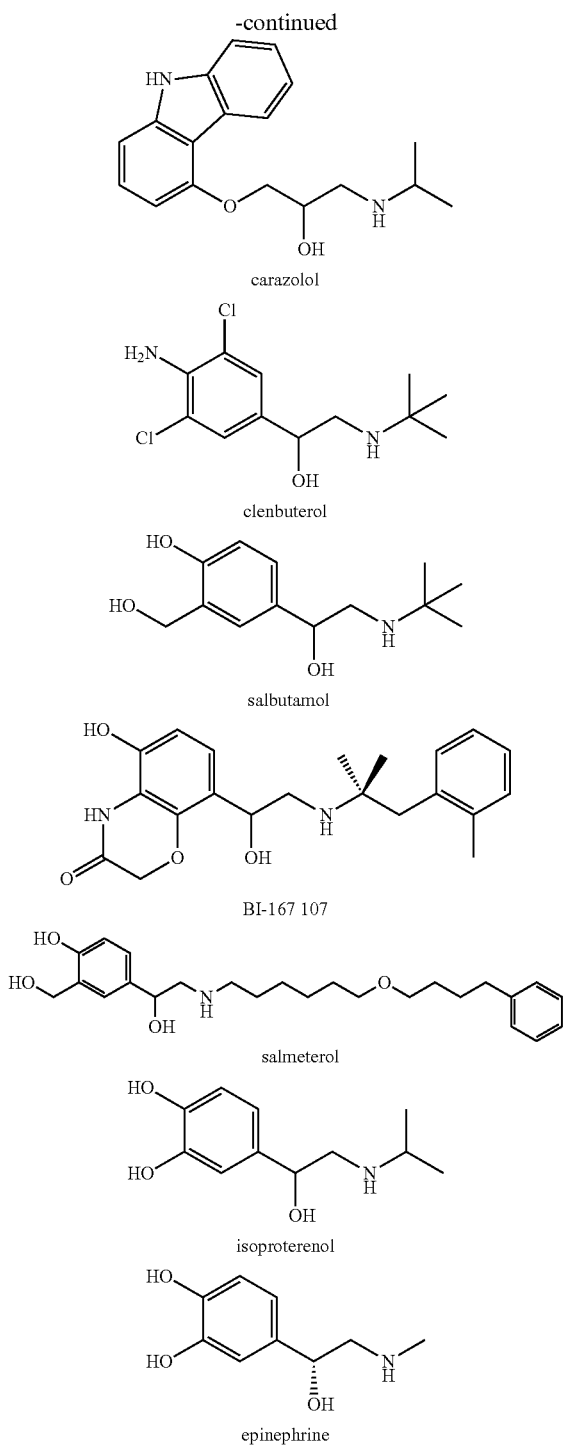

carazolol clenbuterol salbutamol

BI-167 107 salmeterol isoproterenol epinephrine

TABLE 4

| Ligand | $K_i$ (µM) |
| --- | --- |
| salbutamol | 9.05 (p$K_i$: 5.04 ± 0.04) |
| epinephrine (EPI) | 2.89 (p$K_i$: 5.54 ± 0.04) |
| isoproterenol | 0.55 (p$K_i$: 6.26 ± 0.03) |
| clenbuterol | 0.43 (p$K_i$: 6.36 ± 0.02) |
| salmeterol | 0.08 (p$K_i$: 7.11 ± 0.04) |
| ICI-118,151 | 0.02 (p$K_i$: 7.61 ± 0.05) |

All experiments were performed in imaging buffer containing 20 mM HEPES, pH 7.5, 100 mM NaCl, 2 mM CaCl$_2$), 5 mM MgCl2, 2 mM (0.1%) DDM (Anatrace), and 0.2 mM (0.01%) cholesteryl hemisuccinate (Sigma), supplemented with photostabilizing agents (2 mM cyclooctatetraene and 1 mM 4-nitrobenzyl alcohol)[41] and an enzymatic oxygen scavenging system (2 mM protocatechuic acid, 50 nM protocatechuate-3,4-dioxygenase)[42]. Experiments were performed in DDM, a detergent which maintains the $\beta_2$AR in a functional state capable of activating G$_s$. A detergent environment was chosen over lipid nanodiscs because the primary goal of our study is to investigate the effect of ligand efficacy on interactions between the $\beta_2$AR and G$_s$. Performing studies in detergent allows us to monitor interactions between the $\beta_2$AR and G$_s$ without the contribution of receptor-independent interactions between G$_s$ and the lipid bilayer.

Single-molecule fluorescence imaging was conducted at 25° C. using a custom prism-based total internal reflection fluorescence microscope as previously described43. All smFRET data were recorded at 100 ms time resolution (10 frames s$^{-1}$), using custom software implemented in LabView (National Instruments), then processed and analyzed using SPARTAN[43] software as implemented in MATLAB. Acceptor traces were scaled by a constant factor per movie ($\gamma^{-1}$) to correct for unequal apparent fluorophore brightness, where $\gamma$ was calculated as $\gamma=\Delta I_A/\Delta I_D$, where $\Delta I_A$ and $\Delta I_D$ are the changes in the acceptor and donor intensities upon acceptor photobleaching, respectively[44]. FRET trajectories were calculated using the equation FRET=$(1+(I_D/I_A))^{-1}$, where $I_D$ and $I_A$ are the corrected donor and acceptor fluorescence intensities at each frame, respectively. All FRET traces that exhibited: (1) single-step photobleaching; (2) a signal-to-noise ratio (total fluorescence intensity divided by the standard deviation of the same total intensity before photobleaching) above the mean for its dataset; and (3) FRET efficiencies lasting for 10 s were selected for analysis. FRET population contour plots were summed over time into histograms that were fit to a single Gaussian for ligand only data or double Gaussian functions to derive mean FRET efficiency values and distribution full-widths at half-maximum height (FWHM) for the predominant FRET states. The small fraction (~5%) of molecules exhibiting roughly 0.9 FRET were not included in this fitting procedure because they were not responsive to ligand or G$_s$ and thus likely represent non-specifically labelled molecules. Inter-dye distances were estimated from the FRET efficiencies as previously described[45]. The apparent EC$_{50}$ for adrenaline was derived by plotting the shift in the mean FRET efficiency value ($\Delta$FRET) with increasing adrenaline concentration (2 nM-200 µM).

FRET traces were idealized using the segmental K-means algorithm[46] as implemented in QuB software[47], where the FRET values of the two-state model were not fixed during idealization. The resulting FRET state sequences were used in the calculation of state histograms, state-occupancy time trajectories and transition density plots[48]. The rate constants of transitions between states and the corresponding FRET-state lifetimes were estimated by fitting dwell-time survival plots to single exponential decay functions using Origin software (OriginLab). $R^2$ values for all fits were greater than 0.98.

Ranking of agonist molecular efficacies (e, see Table 1 below, column 4) relative to adrenaline in terms of the effective rate of generating G$_s$(GTP) from G$_s$(GDP) (FIG. 5), was estimated by the product of the rates at which $\beta_2$AR achieves active-like conformations ($\eta_1$, Table 1, column 2:

product of apparent $k_{on}$ and $k_{high \to low}$ from Table 2, columns 2 and 3) and apparent $EC_{50}$'s for GDP binding ($\eta_2$, Table 2, column 3), with both values normalized to that of adrenaline.

TABLE 1

Ranking of agonist molecular efficacies ε relative to adrenaline ($\eta_1 \cdot \eta_2$)

| Ligand | $\eta_1$ | $\eta_2$ | ε |
|---|---|---|---|
| CLEN | 0.34 | 0.34 | 0.12 |
| SALM | 0.69 | 0.41 | 0.28 |
| SALB | 0.80 | 0.45 | 0.36 |
| BI | 0.80 | 0.66 | 0.53 |
| ADR | 1.0 | 1.0 | 1.0 |
| ISO | 1.3 | 0.83 | 1.1 |

TABLE 2

Apparent on rate and transition rate from high- to low-FRET states

| Ligand | Apparent $k_{on}$ ($\mu M^{-1} s^{-1}$) | $k_{high \to low}$ ($s^{-1}$) |
|---|---|---|
| ALP | <<0.02 | — |
| CLEN | 0.03 | 0.4 |
| SALM | 0.04 | 0.6 |
| SALB | 0.04 | 0.7 |
| BI | 0.04 | 0.7 |
| EPI | 0.05 | 0.7 |
| ISO | 0.04 | 1.1 |

Note:
Apparent $k_{on}$ and $k_{high \to low}$ values calculated from data used for FIG. 2.

Figure 6:
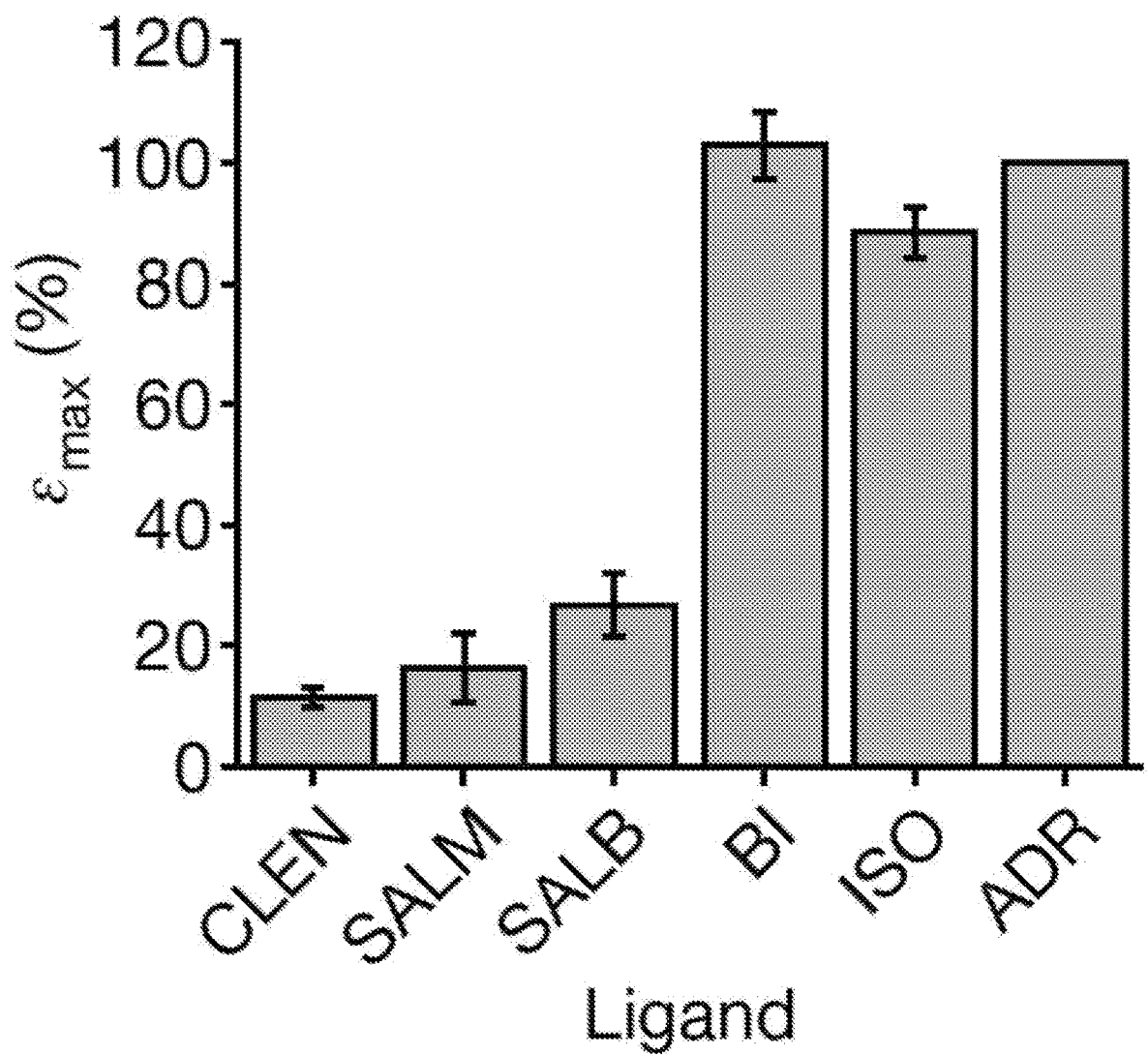
FIG. 6 provides ligand efficacy-based cAMP measurements in living cells, as discussed in the working examples regarding the present technology. Error bars denote s.e.m, 3 replicates; εmax=maximum agonist response.

Regarding the distinct characteristics of BI-167107 (e value of 0.53), according to our present efficacy calculations BI-167107 is indicated as being as efficacious as adrenaline and isoproterenol in both GTP turnover (FIG. 1) and cyclic AMP assays (FIG. 6).

$\beta_2AR$-$G_s$ dissociation experiments. Labelled $\beta_2AR$ in imaging buffer was incubated with saturating a concentration of ligand and a 100-fold molar excess of biotinylated $G_s$ for 30 min at room temperature followed by 30-min apyrase treatment to remove free GDP. Complexes were then surface immobilized as described above and imaged at a frame rate of 0.5 s$^{-1}$ under low laser illumination intensities, where the donor photobleaching rate is relatively slow (<0.1 min$^{-1}$). Here, $\beta_2AR$ exhibited a predominant low FRET state (~0.4; FWHM: ~0.18) in the presence of both partial and full agonists. Consistent with the notion that both complex formation and/or complex stability are ligand dependent, following identical procedures we did not observe sufficient $G_s$-mediated receptor immobilization in the absence of ligand or in the presence of antagonists or inverse agonists to permit analysis. For individual $G_s$-immobilized receptors we observed relatively rare (~1 event per 5 s), transient (<500 ms) fluctuations to higher FRET states. While ligand-dependent distinctions in these $\beta_2AR$ dynamics could not be discerned, such findings suggest that $\beta_2AR$ can access inactive-like conformations while associated with nucleotide-free $G_s$.

The rate of dissociation of ligand-bound, labelled $\beta_2AR$ from $G_s$ was estimated by generating a survival plot tracking the loss of donor fluorescence over time and fitting the data to a single exponential decay function (Table 3, column 3). Control experiments where ligand-bound, labelled $\beta_2AR$ was tethered to the surface via its N-terminal FLAG epitope through biotinylated M1-Fab, where dissociation should not occur over the time course of the experiment, exhibited donor lifetimes that lasted up to approximately 4 times longer (Table 3, column 2), consistent with donor photobleaching.

TABLE 3

Lifetimes of biotin-$G_s$-immobilized and biotin-M1-Fab-immobilized $\beta_2AR$

| | | Biotin-$G_s$-immobilized | | |
|---|---|---|---|---|
| Ligand | M1-immobilized (min) | GNP-free (min) | +GDP (s) | +GTP (s) |
| CLEN | 14.4 ± 2.1 | 8.3 ± 1.3 | 9.8 ± 1.6 | 6.8 ± 0.5 |
| SALB | 18.1 ± 8.4 | 5.0 ± 0.4 | 8.2 ± 0.9 | 6.4 ± 0.1 |
| SALM | 10.8 ± 4.1 | 3.5 ± 1.6 | 9.0 ± 0.4 | 6.6 ± 0.2 |
| BI | 11.0 ± 5.5 | 8.0 ± 3.2 | 9.4 ± 0.6 | 6.2 ± 0.1 |
| ISO | 12.7 ± 3.1 | 6.0 ± 5.2 | 9.8 ± 1.3 | 5.8 ± 0.1 |
| EPI | 13.2 ± 3.4 | 11.2 ± 5.1 | 11.8 ± 1.2 | 6.4 ± 0.1 |

Note:
Lifetime values are shown for biotin-$G_s$-immobilized $\beta_2AR$ in the nucleotide-free state (GNP-free) and after addition of GDP or GTP, and for biotin-M1-Fab-immobilized $\beta_2AR$ in the absence of $G_s$. Data are mean ± s.e.m.

To determine the effect of nucleotides on the rate of dissociation, 30 μM GDP or 100 μM GTP was rapidly injected at the start of data acquisition and the sample was then imaged at 5 frames s$^{-1}$ under the same low intensity illumination regime. The donor fluorescence survival plots determined from these data were best fit to a double exponential function where the fast time component represents the dissociation rate of $\beta_2AR$ from $G_s$ upon nucleotide addition (Table 3, columns 4 and 5). Analogous experiments were performed at higher illumination intensities and faster temporal resolution (10 s$^{-1}$) where the nucleotides were rapidly added at 1 s after the start of imaging. Only FRET traces that exhibited: (1) single-step photobleaching; and (2) FRET efficiencies lasting for 5 s, were selected for analysis. Molecules not exhibiting FRET transitions were excluded from this analysis.

Radioligand binding studies. Saturation binding curves were obtained by incubating purified receptor in the presence of increasing concentrations of the antagonist [$^3$H] dihydroalprenolol (DHA) (PerkinElmer). Care was taken to avoid ligand depletion by using appropriate receptor and DHA concentrations. Binding reactions were set up in the presence of FLAG-sepharose and 2 mM $Ca^{2+}$ and Brandel-harvested after 1.5 h incubation at room temperature. Non-specific binding of DHA was measured by adding 10 μM alprenolol in the binding reaction. Competition binding measurements were performed in a similar way using a DHA concentration slightly above the Kd (as determined by saturation binding) in the presence of increasing concentrations of the full agonist isoproterenol.

Cell-based cAMP assays. For functional testing of the $\beta_2AR$ mutants, we used CHO-K1 Flp-in™ cells (Invitrogen) since they express no functionally detectable endogenous $\beta_2AR$. Cells were cultured in Ham's F-12 medium (Corning Inc.) supplemented with 10% fetal bovine serum (Invitrogen) and 1% penicillin-streptomycin (Corning Inc.). To determine efficacies of ligands without the confound of spare receptors (FIG. 6), we used HEK-293T cells, which endogenously express very low levels of $\beta_2AR$. Cells were cultured in DMEM medium (Corning Inc.) supplemented with 10% fetal bovine serum and 1% penicillin streptomycin.

For transient transfection, 3-4×10$^6$ cells were seeded into 10 cm culture dish plates. The following day, cells were transfected with linear polyethylenimine (PEI; Polysciences, Inc.) at a 1:1 PEI:cDNA ratio. For functional testing of $\beta_2$AR, cells were transfected with the BRET-based cAMP biosensor CAMYEL49 (10 μg), wild-type or mutant $\beta_2$AR constructs (0.025 μg) and pcDNA5/FRT (9.975 μg). To determine efficacy of ligands, cells were transfected with CAMYEL (10 μg) and pcDNA5/FRT (10 μg) (FIG. 6). The medium was changed 24 h after transfection, and after approximately 40 h the cells were washed with PBS, resuspended in 2 ml (CHO) or 4 ml (HEK-293T) BRET buffer (PBS containing 5 mM glucose) and distributed into 96-well OptiPlates (Perkin Elmer Life Sciences) at 45 μl per well. Cells were incubated for 8 min with 5 μM coelenterazine H (NanoLight Technologies) before ligand addition to reach a final well volume of 100 μl. BRET intensities were measured on a Pherastar FS plate reader (BMG) at 2, 5 and 10 min after ligand addition for functional testing and 5 min after ligand addition for the determination of ligand efficacies.

The donor (Rluc and Rluc8) and acceptor (YFP and mVenus) emission was collected at 485 nm and 525 nm, respectively. The BRET signal was calculated as the ratio of light emitted at 525 nm over that emitted at 485 nm. The net BRET ratio was obtained by subtracting baseline BRET. Dose-response curves evaluating the ligand-induced net BRET ratios as a function of ligand concentration were fit by nonlinear regression to a sigmoidal dose-response relationship using Prism 6.0 software (GraphPad Software, San Diego) to determine εmax and $EC_{50}$ values. For the determination of ligand efficacies, εmax values were normalized to that of adrenaline within the same experiment.

Steady-state fluorescence anisotropy measurements. Cy3B*-labelled $\beta_2\Delta$6-N148C/L266C was diluted to a concentration of approximately 7 μM. Samples were excited at 532 nm and emission collected at 575 nm, with a bandpass of 4 nm. The grating factor G was determined experimentally for each measurement using the formula $G(\lambda 575)=I_{HV}/I_{HH}$, where $I_{HV}$ and $I_{HH}$ are the vertical and horizontal emission components, respectively, of horizontally polarized excitation. The anisotropy r was then calculated using the formula $r=(I_{VV}-G\times I_{VH})/(I_{VV}+2G\times I_{VH})$, where G represents the experimentally determined G factor, $I_{VV}$ and $I_{VH}$ the vertical and horizontal emission components, respectively, of vertically polarized excitation[50]. The average anisotropy values were computed from ten replicate measurements.

Fluorescence cross-correlation analysis. Correlation analysis was performed using MATLAB's xcorr function where Pearson's correlations were calculated for donor and acceptor fluorescence channels from individual traces included in the histograms, excluding a small subset with unusual behavior (~10%) by requiring that the Pearson's correlation coefficient in each trace was greater than −0.5. Only frames with a FRET efficiency>0.18 within the first 100 frames were considered to avoid any contributions of fluorophore dark states. Time-dependent changes in anticor-related fluorescence fluctuations were plotted as population histograms of Pearson's correlations in the presence of ligands at zero lag and when the donor trace was shifted relative to the acceptor by the indicated number of frames (lag time).

While rapid photoblinking events (<100 ms) may contribute to fluorescence anticorrelation, this is not consistent with the unimodal distribution of fluorescence correlation for adrenaline-bound $\beta_2$AR, where the entire ensemble of individual molecules has negative fluorescence correlation that relaxes to zero at longer lag times. Moreover, photoblinking is generally proportional to the number of photons emitted[51,52], and would be expected to have a greater effect on samples with higher acceptor emission intensities (higher FRET).

At first glance, our ligand-only FRET investigations appear to contradict previous DEER studies that show isoproterenol and BI-167107 promote larger-scale outward displacements of TM6, resulting in a mixture of inactive and active conformations in equilibrium[11]. However, DEER experiments were performed on frozen samples (t=80 K) and do not provide information on the exchange rates between different conformations, whereas the present smFRET analyses reflect information about the exchange rates between the underlying states sampled by the system.

Recent ensemble $^{19}$F-NMR studies[11] and single-molecule fluorescence intensity investigations[16] have also observed conformational transitions in the $\beta_2$AR on much slower time scales (~0.5-5 s$^{-1}$) than our correlation analyses suggest. Such differences may reflect distinctions in the nature of the probes utilized as well as the experimental conditions and $\beta_2$AR constructs employed. For instance, both studies employed probes that detect changes in environment, not distance. Hence, the nature of the exchange process measured may relate to conformational changes that are not associated with large displacements of TM6 relative to TM4. In addition, the dynamics reported by Lamichhane and colleagues[16] may also be influenced by the thermostabilizing mutations and truncations in their $\beta_2$AR construct.

Simulation of single-molecule fluorescence and FRET traces. For each condition, 3,000 noiseless, continuous-time state sequences were simulated[53] according to a two-state kinetic model with mean FRET values of 0.75 (inactive) and 0.55 (active), active-to-inactive state transition rate constants that were varied from 100 to 10,000 s$^{-1}$ and the reverse transition rate made constant at 100 s$^{-1}$. These sequences were binned to 100 ms time resolution to obtain smFRET traces. Noiseless donor and acceptor fluorescence traces ($I_A$ and $I_D$, respectively) were calculated from FRET values according to the equations $I_D=T\cdot(1-FRET)$ and $I_A=\gamma\cdot T\cdot FRET$, where T is the target total fluorescence intensity (1,300 photons) and $\gamma$ is the apparent brightness of the acceptor relative to the donor (0.14). To simulate uncertainty resulting from photon statistics, values were randomly drawn from Poisson distributions centered at the expected fluorescence intensities in each frame. Gaussian-distributed noise was added to both fluorescence channels to simulate background noise. Traces terminated in simulated photobleaching events, with an exponential time constant of 20 s. The traces were then subjected to the same analysis procedure as the experimental data.

Molecular dynamics simulations of $\beta_2$AR with activated Cy3B* and activated Cy7* fluorophores. The initial model of the $\beta_2$AR-BI/$G_s$ protein construct, composed of the $\beta_2$AR with the BI-167107 agonist and the heterotrimeric $G_s$ protein, was based on the crystal structure of $\beta_2$AR-BI-167107-$G_s$ complex[6] (Protein Data Bank (PDB) accession 3SN6; Rasmussen, S. G. et al. Crystal structure of the $\beta_2$ adregenic receptor-$G_s$ protein complex. Nature 477, 549-555 (2011), incorporated herein by reference). The initial structure of the inactive receptor model ($\beta_2$AR-CZ) was based on the crystal structure of the $\beta_2$AR bound to carazolol[54] (PDB code 2RH1; Cherezov, V. et al. High-resolution crystal structure of an engineered human $\beta_2$-Adregenic G Protein-Coupled Receptor. Science 318, 1258-1265 (2007)). Three mutations were included in the $\beta_2$AR structure (N148C, L266C and C341L) and part of the missing ICL3 loop was modeled as an unstructured segment (the segment S246-L259 was not included). The fluorophores Cy7* and the Cy3B* were attached at positions 148[4.40] and 266[6.28], respectively. Post-translational modifications for the $\beta_2$AR-BI/$G_s$ system at the G$\alpha$ (palmitoylation and myristoylation) and G$\gamma$ (palmitoylation) subunits were included.

For the simulations, the models were originally surrounded by 361 DDM detergent molecules, where some molecules were initially placed at the vicinity of the protein complex while others were placed at larger distances from the protein (bulk positions). Some detergent molecules were removed from the systems based on steric considerations. The entire systems were solvated in explicit water and 0.15 M NaCl[55]. The final system contains approximately 430 thousand and 330 thousand atoms for the $\beta_2$AR-BI/$G_s$ and $\beta_2$AR-CZ systems, respectively.

Unbiased all-atom molecular dynamics simulations of the $\beta_2$AR-BI/$G_s$ and $\beta_2$AR-CZ systems described above were carried out using NAMD[56] and the all-atom CHARMM27 force field with CMAP corrections[57]. The parameters for the ligands carazolol and BI-167107 were automatically assigned by analogy with the CHARMM force field[58,59]. The parameters for the fluorophores were also obtained partially from similar sources but additional electronic structure calculations were included to generate a complete set of parameters consistent with CHARMM[58,59]. Langevin dynamics and the Nose-Hoover Langevin piston were used to perform the simulations at a constant temperature of 310 K and at 1 atm constant pressure[60]. A 2.0 fs time step was utilized and the bond lengths[57] involving hydrogen atoms were constrained by the SHAKE algorithm[61]. PME techniques using a grid of spacing<1.0 Å in each dimension were used to evaluate the electrostatics of the systems[62].

Discussion of Certain Aspects of Data and Results

Figure 3:
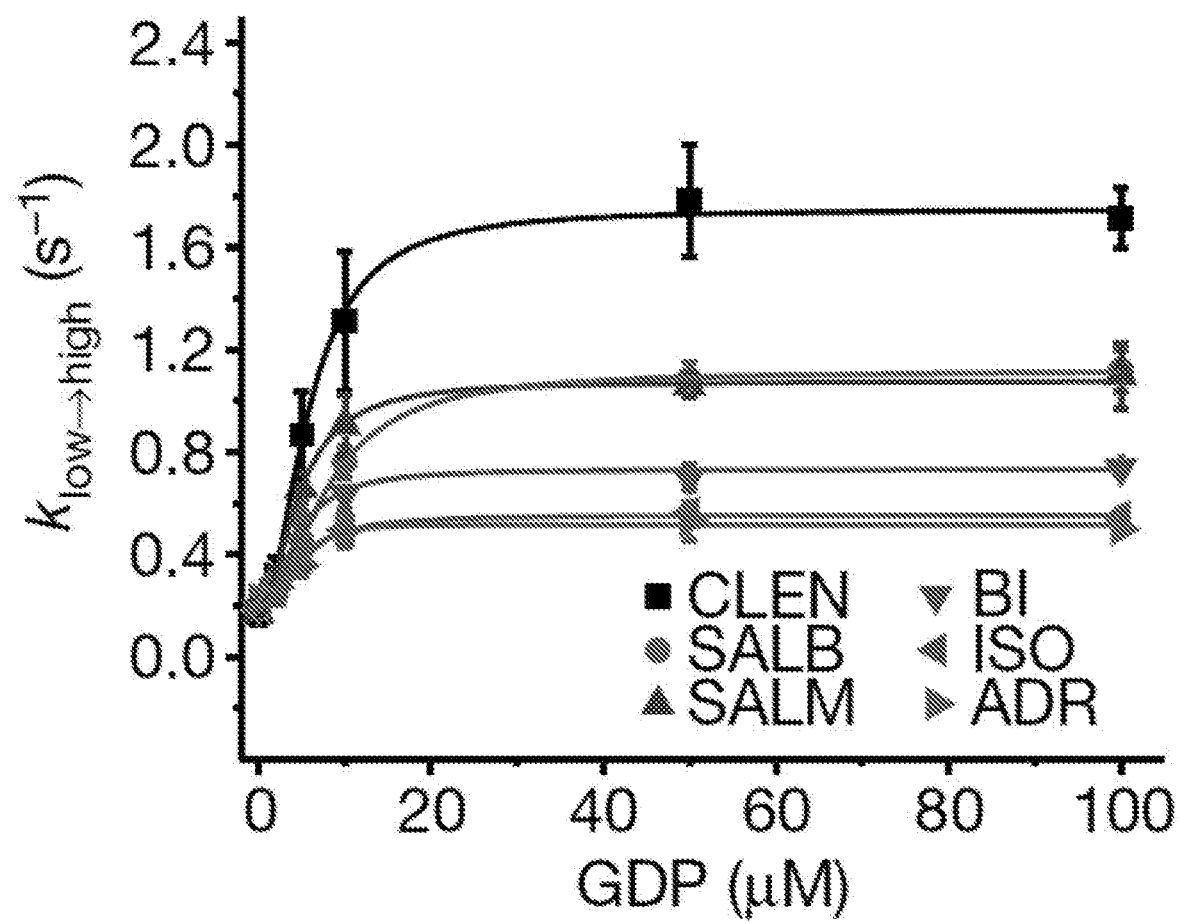
FIG. 3 provides the transition rates from low- to high-FRET states ($k_{low \rightarrow high}$) with agonists (CLEN, SALB, SALM, BI, ISO, ADR), $G_s$, and increasing GDP concentrations, as discussed in the working examples regarding the present technology. Error bars denote s.d. (2 replicates).

The effect of ligand efficacy on the allosteric link between $\beta_2$AR and $G_s$, and its role in nucleotide exchange was further examined in steady-state experiments using M1-immobilized receptor in the presence of activating ligands, nucleotide and 8 $\mu$M $G_s$ (FIG. 3). Under such conditions, $G_s$ dissociation events are expected to be slow (around 0.1-0.2 s$^{-1}$; Table 3), while dynamic processes within the $\beta_2$AR-$G_s$ complex should occur rapidly. $\beta_2$AR-$G_s$ complexes can exhibit three distinct FRET states: (1) a low-FRET, nucleotide-free state (0.4); (2) a high-FRET, agonist-bound (0.64) or partial agonist-bound (0.72) state while the receptor remains associated with $G_s$; and (3) an intermediate-FRET state (about 0.5) reflecting a GDP-bound $\beta_2$AR-$G_s$ complex with a distinct mode of interaction between TM6 and the $\alpha$ 5-helix that is relatively short lived. Because the two lower-FRET states can be seen clearly only in pre-steady-state experiments, the steady-state data was analyzed as a two-state system in which states (1) and (3) are collapsed into a single, broadly defined (0.4-0.5) low-FRET state.

To learn about the rate-limiting features of $\beta_2$AR-$G_s$ complex formation, the rates of low- and high-FRET state formation ($k_{high \to low}$ and $k_{low \to high}$, respectively) were examined over a range of GDP concentrations. As expected for binding of a GDP-bound $G_s$ heterotrimer, $k_{high \to low}$ was largely independent of GDP concentration for all agonists. By contrast, $k_{low \to high}$ increased with GDP and plateaued at concentrations above 20 $\mu$M (FIG. 3). Consistent with TM6 dynamics occurring within the $\beta_2$AR-$G_s$ complex, the maximum rates exiting low FRET were approximately 5-15-fold more rapid than the apparent $G_s$ dissociation rate (Table 3). The rank order of the low- to high-FRET state transition was: clenbuterol, salbutamol, salmeterol, BI-167107, isoproterenol and adrenaline. Given that GDP binding to the nucleotide-free $\beta_2$AR-$G_s$ complex is rapid, we conclude that the transition out of low-FRET states into high-FRET states is rate-limited by one or more ligand-dependent processes within the $\beta_2$AR-$G_s$(GDP) complex.

As low FRET includes both nucleotide-free and GDP-bound complexes, we speculated that the slower rates of return to high FRET observed for full agonists (FIG. 3) may reflect higher proportions of the relatively stable nucleotide-free state. We therefore undertook an evaluation of differences in the proportion of nucleotide-free $\beta_2$AR-$G_s$ complexes in the presence of distinct agonists using the experimentally observed mean value of the low-FRET state as a function of GDP concentration. This analysis revealed that the low-FRET state values observed at saturating GDP concentration (100 $\mu$M) were considerably lower for full agonists compared to partial agonists, more closely approximating the FRET value (~0.4) observed for the nucleotide-free $\beta_2$AR-$G_s$ complex. Consistent with GDP binding promoting a return to the high-FRET state, increasing GDP concentrations increased the mean values of the low-FRET states, while decreasing their time-averaged occupancies. The concentration dependence of these effects revealed that full agonists exhibited EC$_{50}$ values that were approximately 2-3-fold higher than for partial agonists. These data suggest that $\beta_2$AR-$G_s$ complexes exhibit higher affinity for GDP when bound to partial agonists than when bound to full agonists. They also support the notion that low-FRET states represent a mixture of nucleotide-free and GDP-bound $\beta_2$AR-$G_s$ configurations, where complexes activated by full agonists spend more time on average in the relatively stable, nucleotide-free state. These findings may help to explain why adrenaline promotes a greater extent of [$^3$H]GDP release from a $\beta_2$AR compared to salbutamol[27], despite both agonists promoting low-FRET states at similar rates (FIG. 2). As the rates of GDP binding to nucleotide-free $\beta_2$AR-$G_s$ complexes are rapid, and appear indistinguishable at the present time resolution, we conclude that more efficacious agonists increase the probability of GDP release and thus the likelihood that nucleotide-free states are achieved.

Figure 4:
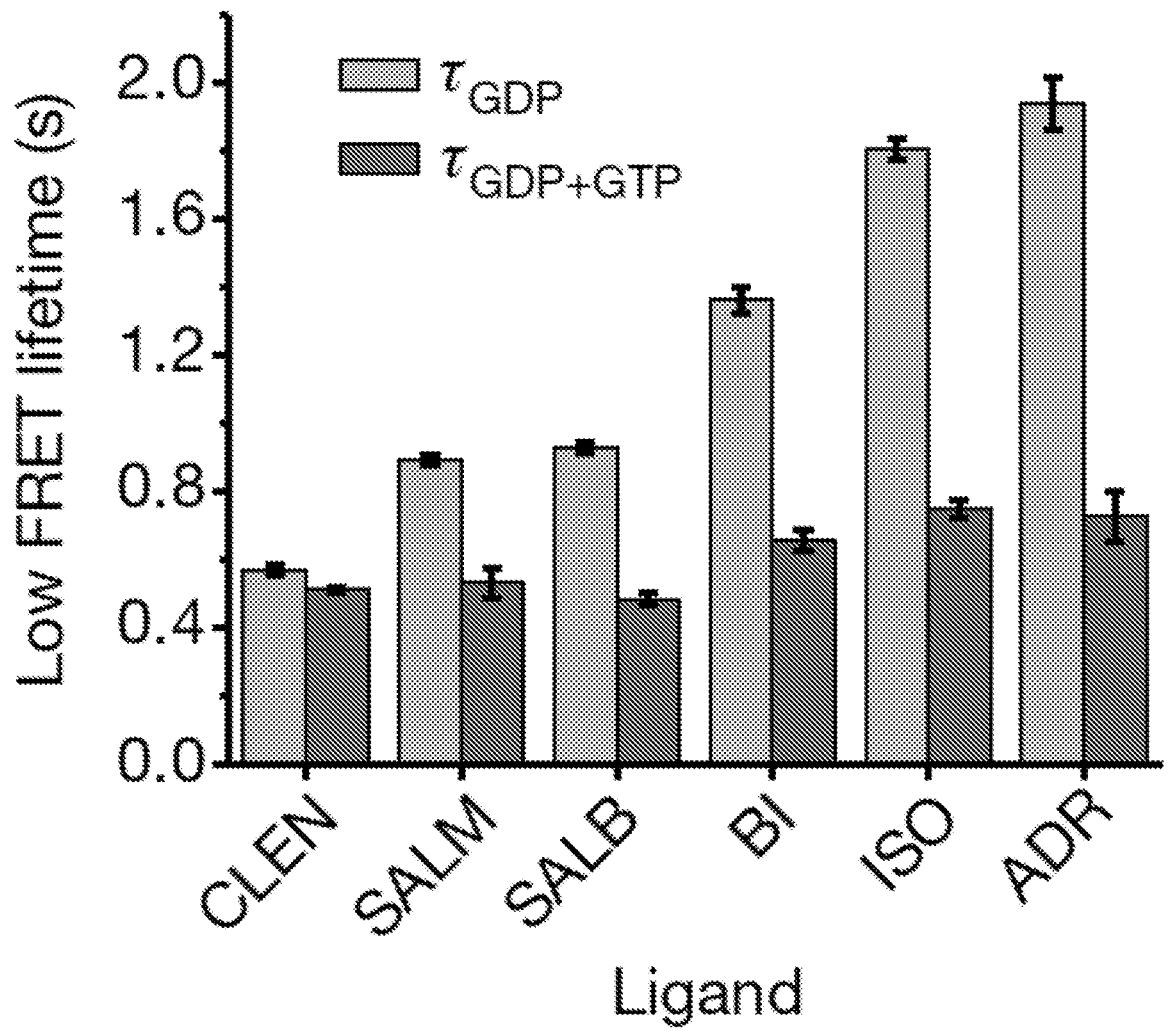
FIG. 4 provides nistograms of low-FRET state lifetimes (r) for each agonists (CLEN, SALB, SALM, BI, ISO, ADR) with $G_s$ and saturating GDP (light grey) or saturating GTP and GDP (dark grey), as discussed in the working examples regarding the present technology. Error bars denote s.d. (2 replicates).
Figure 8:
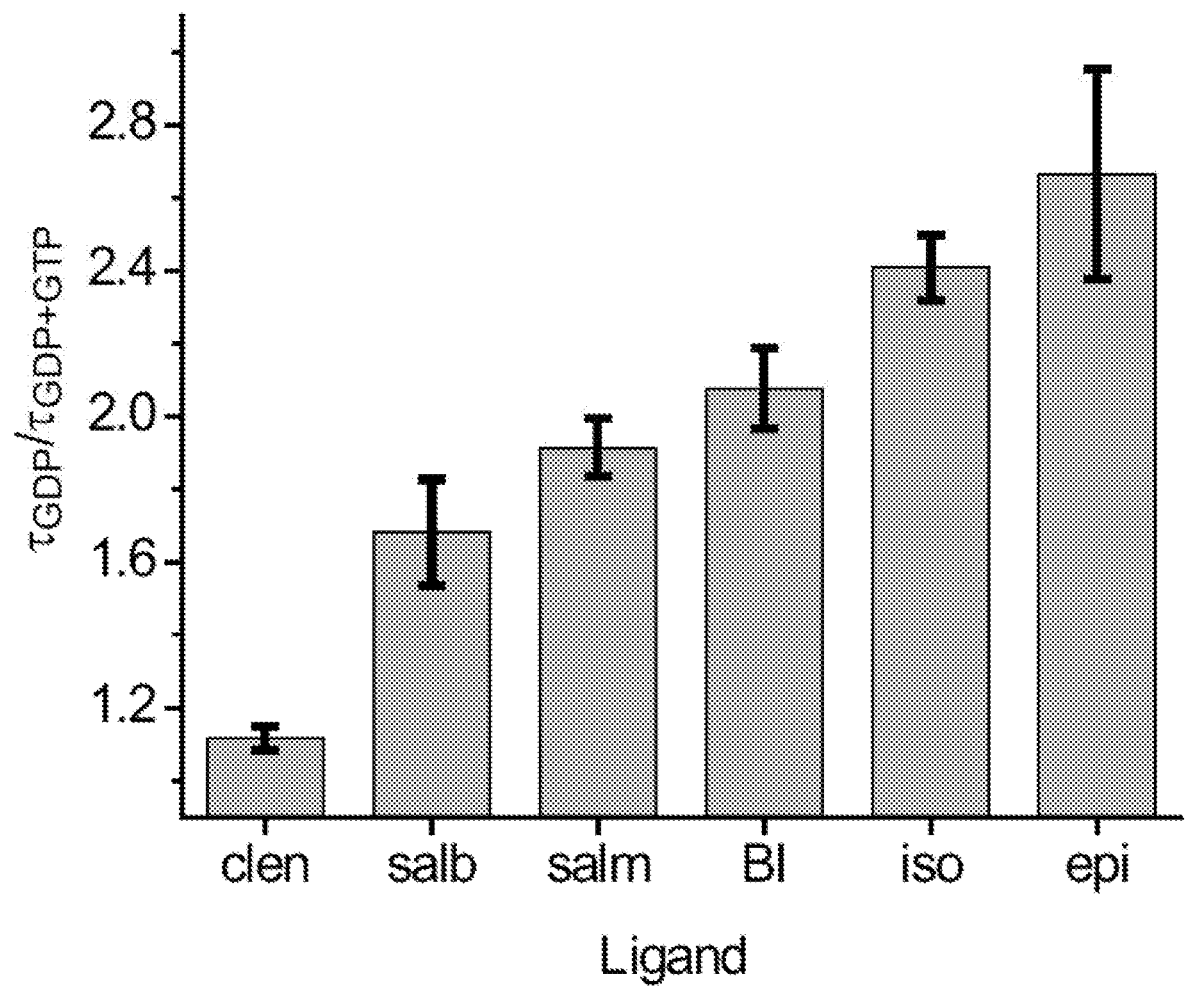
FIG. 8 provides the ratio of the low-FRET state lifetime of $β_2AR$ in the presence of saturating $G_s$ and GDP (τGDP) over the low-FRET state lifetime in saturating GTP plus 30 µM GDP (τGDP+GTP)(see FIG. 4) for different agonists. All error bars represent s.d. from two replicates.

To test this model directly, analogous GTP titrations were performed in the presence of a fixed, saturating GDP concentration (30 $\mu$M). As anticipated, the transition rate from low-to-high FRET ($k_{low \to high}$) was in all cases specifically increased at even the lowest GTP concentrations tested (100 nM). While the absolute values of $k_{low \to high}$ were greater for partial agonists in the presence of GTP, the fold increase in rate, and hence the magnitude reduction in low-FRET state lifetime, correlated with ligand efficacy in the order: adrenaline, isoproterenol, BI-167107, salmeterol, salbutamol and clenbuterol (FIG. 8). Taken together with the rapid rates of GDP and GTP binding to nucleotide-free $\beta_2$AR-$G_s$ complexes, we conclude that the relatively short-lived, active-like, low-FRET $\beta_2$AR conformations observed in the presence of partial agonists (FIG. 4) predominantly reflect failed attempts at nucleotide release, and that full agonists more efficiently promote relatively long-lived, nucleotide-free configurations. Hence, ligands with greater efficacy preferentially promote GDP release, and under competitive conditions, rapid and efficient GTP loading to the subpopulation of nucleotide-free complexes. The more rapid return of $\beta_2$AR-$G_s$(GTP) complexes to high-FRET states after GTP loading argues that the terminal phosphate of GTP lowers the barrier for the rate-limiting conformational transition that enables the return of TM6 to its position adjacent to the helix bundle. This distinction may reflect GTP-specific effects on $G_s$ heterotrimer stability.

Ligand-activated $G_s$ binding, nucleotide exchange, and $G_s$ release were thus examined from the perspective of time-dependent changes in $\beta_2$AR conformation. The results illuminate the established concept of ligand efficacy in terms of a specific kinetic framework for the activation pathway. Quantifying the ligand-dependence of both the rate and the efficiency of $G_s$ coupling in the presence of physiological GDP concentrations revealed that the process is achieved by rate-limiting conformational processes intrinsic to the $\beta_2AR$-$G_s$ complex (FIG. 2). Although the nature of the interactions preceding excursions to low-FRET, active-like conformations are not presently known, the rates evidenced at saturating $G_s$ concentration (FIG. 2) suggest ligand-specific effects on the probability that $G\alpha_s$ productively engages the intracellular face of $\beta_2AR$ after the complex has formed. The molecular events underpinning these early activation steps minimally include the remodeling of the $\beta6\alpha$ 5 loop proximal to the $G\alpha_s$ switch regions, and translation and rotation of the $\alpha$ 5 helix of Ga away from the GDP binding pocket towards the intracellular vestibule in $\beta_2AR$ created by the outward movement of TM6[28-35].

Figure 5:
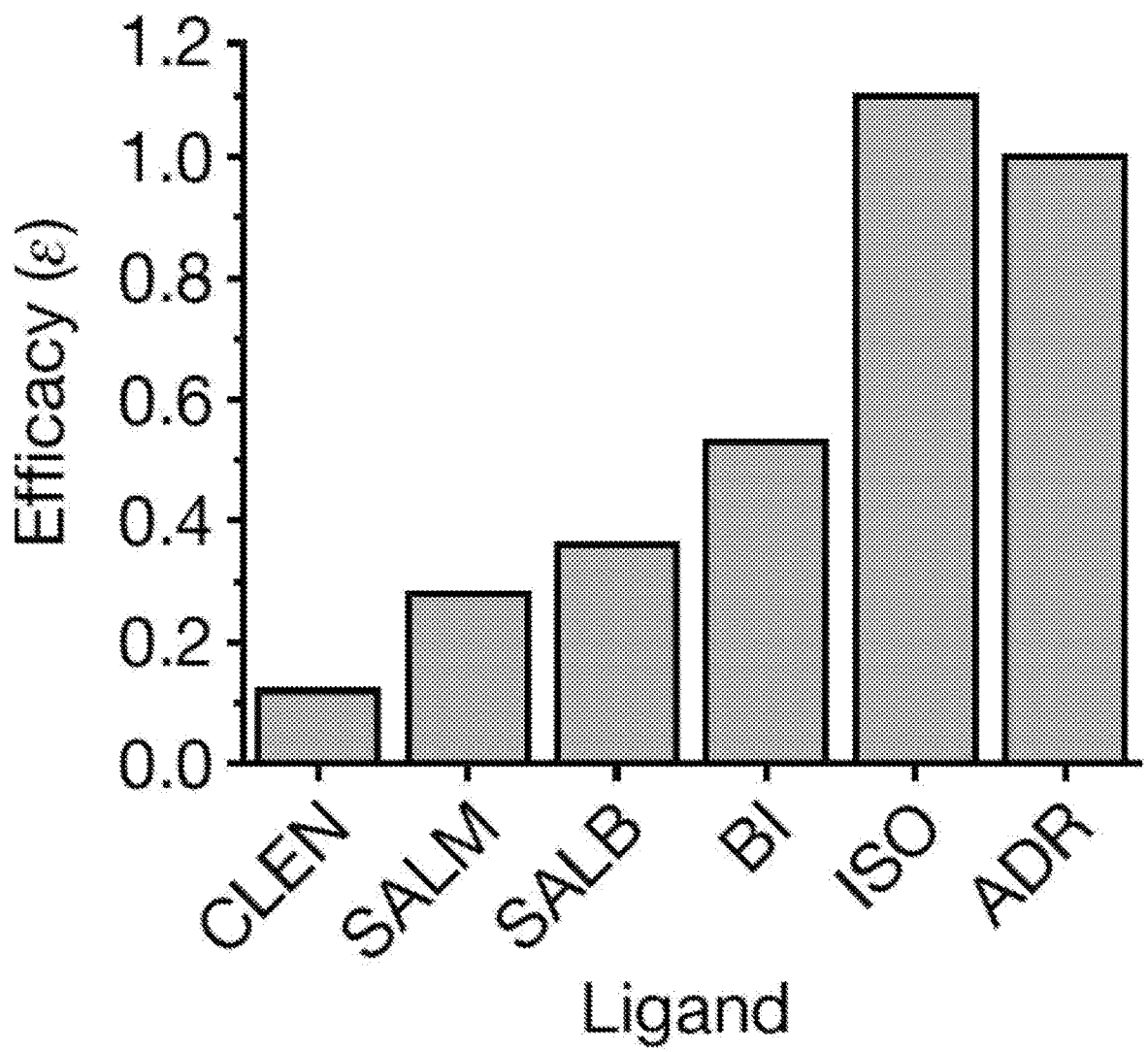
FIG. 5 provides a ranking of agonist molecular efficacies (E) relative to adrenaline in terms of the effective rate of generating $G_s$(GTP) from $G_s$(GDP), as discussed in the working examples regarding the present technology.

The apparent differences in initial engagement and the rate-limiting conformational changes leading to active-like, lower-FRET states (FIG. 2, Table 2), provide an estimate of the relative ligand-dependent efficiencies ($\eta_1$) in these hidden early steps. A second determinant of ligand efficacy ($\eta_2$)—which likely arises from differences in how efficiently the $\alpha$ 5 helix C terminus of $G\alpha_s$ productively engages, and forms stabilizing interactions, with the intracellular $\beta_2AR$ surface[34]—may be estimated from the propensity of full agonists to more effectively promote GDP release. Using the normalized parameters ($\eta_1$, $\eta_2$), the efficacies of activating ligands relative to adrenaline ($\varepsilon$) can be ranked in terms of their effective rates of generating $G_s(GTP)$ from $G_s(GDP)$ (FIG. 5). In doing so, isoproterenol is predicted to be around eight times more efficacious than clenbuterol. While these predictions suggest greater efficacy differences than inferred from in vitro GTP turnover assays (FIG. 1), they are in close agreement with cyclic AMP production in living cells (FIG. 6). Ligand-specific disparities in our calculated values versus the measured ligand efficacy values may reflect agonist-specific differences in GTP binding rates and/or affinities.

REFERENCES

1. Pierce, K. L., Premont, R. T. & Lefkowitz, R. J. Seven-transmembrane receptors. *Nat. Rev. Mol. Cell Biol.* 3, 639-650 (2002).
2. Vilardaga, J. P. et al. GPCR and G proteins: drug efficacy and activation in live cells. *Mol. Endocrinol.* 23, 590-599 (2009).
3. Kenakin, T. New concepts in pharmacological efficacy at 7TM receptors: IUPHAR review 2. *Br. J. Pharmacol.* 168, 554-575 (2013).
4. Manglik, A. & Kobilka, B. The role of protein dynamics in GPCR function: insights from the β2AR and rhodopsin. *Curr. Opin. Cell Biol.* 27, 136-143 (2014).
5. Baker, J. G. The selectivity of β-adrenoceptor agonists at human β1-, β2- and β3-adrenoceptors. *Br. J. Pharmacol.* 160, 1048-1061 (2010).
6. Rasmussen, S. G. et al. Crystal structure of the R 2 adrenergic receptor-Gs protein complex. *Nature* 477, 549-555 (2011).
7. Kruse, A. C. et al. Activation and allosteric modulation of a muscarinic acetylcholine receptor. *Nature* 504, 101-106 (2013).
8. Huang, W. et al. Structural insights into μ-opioid receptor activation. *Nature* 524, 315-321 (2015).
9. Carpenter, B., Nehmé, R., Warne, T., Leslie, A. G. & Tate, C. G. Structure of the adenosine A2A receptor bound to an engineered G protein. *Nature* 536, 104-107 (2016).
10. Yao, X. J. et al. The effect of ligand efficacy on the formation and stability of a GPCR-G protein complex. *Proc. Natl Acad. Sci. USA* 106, 9501-9506 (2009).
11. Manglik, A. et al. Structural insights into the dynamic process of β2-adrenergic receptor signaling. *Cell* 161, 1101-1111 (2015).
12. Nygaard, R. et al. The dynamic process of β2-adrenergic receptor activation. *Cell* 152, 532-542 (2013).
13. Cooper, M. et al. Cy3B: improving the performance of cyanine dyes. *J. Fluoresc.* 14, 145-150 (2004).
14. Vafabakhsh, R., Levitz, J. & Isacoff, E. Y. Conformational dynamics of a class C G-protein-coupled receptor. *Nature* 524, 497-501 (2015).
15. Kim, H. D. et al. Mg2+-dependent conformational change of RNA studied by fluorescence correlation and FRET on immobilized single molecules. *Proc. Natl Acad. Sci. USA* 99, 4284-4289 (2002).
16. Lamichhane, R. et al. Single-molecule view of basal activity and activation mechanisms of the G protein-coupled receptor β2AR. *Proc. Natl Acad. Sci. USA* 112, 14254-14259 (2015).
17. Bond, R. A. et al. Physiological effects of inverse agonists in transgenic mice with myocardial overexpression of the β2-adrenoceptor. *Nature* 374, 272-276 (1995).
18. Ferguson, A. et al. Functional dynamics within the human ribosome regulate the rate of active protein synthesis. *Mol. Cell* 60, 475-486 (2015).
19. Galés, C. et al. Real-time monitoring of receptor and G-protein interactions in living cells. *Nat. Methods* 2, 177-184 (2005).
20. Ernst, O. P., Gramse, V., Kolbe, M., Hofmann, K. P. & Heck, M. Monomeric G protein-coupled receptor rhodopsin in solution activates its G protein transducing at the diffusion limit. *Proc. Natl Acad. Sci. USA* 104, 10859-10864 (2007).
21. Traut, T. W. Physiological concentrations of purines and pyrimidines. *Mol. Cell. Biochem.* 140, 1-22 (1994).
22. Hein, P. et al. Gs activation is time-limiting in initiating receptor-mediated signaling. *J. Biol. Chem.* 281, 33345-33351 (2006).
23. Galés, C. et al. Probing the activation-promoted structural rearrangements in preassembled receptor-G protein complexes. *Nat. Struct. Mol. Biol.* 13, 778-786 (2006).
24. Qin, K., Dong, C., Wu, G. & Lambert, N. A. Inactive-state preassembly of Gq-coupled receptors and Gq heterotrimers. *Nat. Chem. Biol.* 7, 740-747 (2011).
25. Westfield, G. H. et al. Structural flexibility of the Gα s α-helical domain in the β2-adrenoceptor Gs complex. *Proc. Natl Acad. Sci. USA* 108, 16086-16091 (2011).
26. Damian, M. et al. Ghrelin receptor conformational dynamics regulate the transition from a preassembled to an active receptor:Gq complex. *Proc. Natl Acad. Sci. USA* 112, 1601-1606 (2015).
27. Murayama, T. & Ui, M. [3H]GDP release from rat and hamster adipocyte membranes independently linked to receptors involved in activation or inhibition of adenylate cyclase. Differential susceptibility to two bacterial toxins. *J. Biol. Chem.* 259, 761-769 (1984).
28. Ceruso, M. A., Periole, X. & Weinstein, H. Molecular dynamics simulations of transducin: interdomain and front to back communication in activation and nucleotide exchange. *J. Mol. Biol.* 338, 469-481 (2004).

29. Herrmann, R. et al. Sequence of interactions in receptor-G protein coupling. *J. Biol. Chem.* 279, 24283-24290 (2004).
30. Herrmann, R. et al. Rhodopsin-transducin coupling: role of the Gα C-terminus in nucleotide exchange catalysis. *Vision Res.* 46, 4582-4593 (2006).
31. Oldham, W. M., Van Eps, N., Preininger, A. M., Hubbell, W. L. & Hamm, H. E. Mechanism of the receptor-catalyzed activation of heterotrimeric G proteins. *Nat. Struct. Mol. Biol.* 13, 772-777 (2006).
32. Kapoor, N., Menon, S. T., Chauhan, R., Sachdev, P. & Sakmar, T. P. Structural evidence for a sequential release mechanism for activation of heterotrimeric G proteins. *J. Mol. Biol.* 393, 882-897 (2009).
33. Kaya, A. I. et al. A conserved phenylalanine as a relay between the α 5 helix and the GDP binding region of heterotrimeric Gi protein a subunit. *J. Biol. Chem.* 289, 24475-24487 (2014).
34. Dror, R. O. et al. Signal transduction. Structural basis for nucleotide exchange in heterotrimeric G proteins. *Science* 348, 1361-1365 (2015).
35. Flock, T. et al. Universal allosteric mechanism for Ga activation by GPCRs. *Nature* 524, 173-179 (2015).
36. Zheng, Q. S. et al. Electronic tuning of self-healing fluorophores for live-cell and single molecule imaging. *Chem Sci* 8, 755-762 (2017).
37. Kobilka, B. K. Amino and carboxyl terminal modifications to facilitate the production and purification of a G protein-coupled receptor. *Anal Biochem* 231, 269-271 (1995).
38. Mondal, S., Hsiao, K. & Goueli, S. A. A Homogenous Bioluminescent System for Measuring GTPase, GTPase Activating Protein, and Guanine Nucleotide Exchange Factor Activities. *Assay Drug Dev Technol* 13, 444-455 (2015).
39. Fairhead, M., Krndija, D., Lowe, E. D. & Howarth, M. Plug-and-play pairing via defined divalent streptavidins. *J Mol Biol* 426, 199-214 (2014).
40. Blanchard, S. C., Gonzalez, R. L., Kim, H. D., Chu, S. & Puglisi, J. D. tRNA selection and kinetic proofreading in translation. *Nat Struct Mol Biol* 11, 1008-1014 (2004).
41. Dave, R., Terry, D. S., Munro, J. B. & Blanchard, S. C. Mitigating unwanted photophysical processes for improved single-molecule fluorescence imaging. *Biophys J* 96, 2371-2381 (2009).
42. Aitken, C. E., Marshall, R. A. & Puglisi, J. D. An oxygen scavenging system for improvement of dye stability in single-molecule fluorescence experiments. *Biophys J* 94, 1826-1835 (2008).
43. Juette, M. F. et al. Single-molecule imaging of non-equilibrium molecular ensembles on the millisecond timescale. *Nat Methods* 13, 341-344 (2016).
44. Roy, R., Hohng, S. & Ha, T. A practical guide to single-molecule FRET. *Nat Methods* 5, 507-516 (2008).
45. Zhao, Y. et al. Single-molecule dynamics of gating in a neurotransmitter transporter homologue. *Nature* 465, 188-193 (2010).
46. Qin, F. Restoration of single-channel currents using the segmental k-means method based on hidden Markov modeling. *Biophys J* 86, 1488-1501 (2004).
47. Nicolai, C. & Sachs, F. Solving ion channel kinetics with the QuB software. *Biophysical Reviews and Letters* 8, 191-211 (2013).
48. McKinney, S. A., Joo, C. & Ha, T. Analysis of single-molecule FRET trajectories using hidden Markov modeling. *Biophys J* 91, 1941-1951 (2006).
49. Jiang, L. I. et al. Use of a cAMP BRET sensor to characterize a novel regulation of cAMP by the sphingosine 1-phosphate/G13 pathway. *J Biol Chem* 282, 10576-10584 (2007).
50. Lakowicz, J. R. *Principles of Fluorescence Spectroscopy.* 3rd edn, (Springer, 2006).
51. Blanchard, S. C., Kim, H. D., Gonzalez, R. L., Jr., Puglisi, J. D. & Chu, S. tRNA dynamics on the ribosome during translation. *Proc Natl Acad Sci USA* 101, 12893-12898 (2004).
52. Bates, M., Blosser, T. R. & Zhuang, X. W. Short-range spectroscopic ruler based on a single-molecule optical switch. *Phys Rev Lett* 94 (2005).
53. Blatz, A. L. & Magleby, K. L. Correcting single channel data for missed events. *Biophys J* 49, 967-980 (1986).
54. Cherezov, V. et al. High-resolution crystal structure of an engineered human beta2-adrenergic G protein-coupled receptor. *Science* 318, 1258-1265 (2007).
55. Perez-Aguilar, J. M., Shan, J., LeVine, M. V., Khelashvili, G. & Weinstein, H. A functional selectivity mechanism at the serotonin-2A GPCR involves ligand-dependent conformations of intracellular loop 2. *J Am Chem Soc* 136, 16044-16054 (2014).
56. Phillips, J. C. et al. Scalable molecular dynamics with NAMD. *J Comput Chem* 26, 1781-1802 (2005).
57. Mackerell, A. D., Jr., Feig, M. & Brooks, C. L., 3rd. Extending the treatment of backbone energetics in protein force fields: limitations of gas-phase quantum mechanics in reproducing protein conformational distributions in molecular dynamics simulations. *J Comput Chem* 25, 1400-1415 (2004).
58. Vanommeslaeghe, K. et al. CHARMM general force field: A force field for drug-like molecules compatible with the CHARMM all-atom additive biological force fields. *J Comput Chem* 31, 671-690 (2010).
59. Yesselman, J. D., Price, D. J., Knight, J. L. & Brooks, C. L., 3rd. MATCH: an atomtyping toolset for molecular mechanics force fields. *J Comput Chem* 33, 189-202 (2012).
60. Feller, S. E., Zhang, Y. H., Pastor, R. W. & Brooks, B. R. Constant-Pressure Molecular-Dynamics Simulation—the Langevin Piston Method. *J Chem Phys* 103, 4613-4621 (1995).
61. Ryckaert, J. P., Ciccotti, G. & Berendsen, H. J. C. Numerical-Integration of Cartesian Equations of Motion of a System with Constraints—Molecular-Dynamics of N-Alkanes. *J Comput Phys* 23, 327-341 (1977).
62. Darden, T., York, D. & Pedersen, L. Particle Mesh Ewald—an N·Log(N) Method for Ewald Sums in Large Systems. *J Chem Phys* 98, 10089-10092 (1993).

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A method for providing a molecular efficacy of a ligand, the method comprising
  normalizing an effective rate of generating $G_s(GTP)$ from $G_s(GDP)$ provided by the ligand to an effective rate of adrenaline in generating $G_s(GTP)$ from $G_s(GDP)$ to provide a normalized value $\eta_1$; and
  normalizing an apparent $EC_{50}$ for GDP binding of the ligand to an apparent $EC_{50}$ for GDP binding of adrenaline to provide a normalized value $\eta_2$;
  wherein a value greater than 1.0 for the multiple of $\eta_1$ and $\eta_2$ indicates the ligand is more efficacious than adrenaline.

B. The method of Paragraph A, wherein the method further comprises
  single-molecule fluorescence resonance energy transfer ("smFRET") imaging of a complex of $G_s$ with Cy3B*/Cy7*-labelled $\beta_2\Delta 6$-N148C/L266C ("labelled $B_2AR$") in the presence of a saturating concentration of the ligand, a concentration of $G_s$, and a concentration of apyrase.

C. The method of Paragraph A or Paragraph B, wherein the method further comprises
  smFRET of Cy3B*/Cy7*-labelled $\beta_2\Delta 6$-N148C/L266C in the presence of a saturating concentration of the ligand, a concentration of GDP, and two or more different concentrations of $G_s$;
  wherein at least two of the two or more different concentrations of $G_s$ are each below a saturating concentration of $G_s$.

D. The method of Paragraph B or Paragraph C, wherein the smFRET imaging precedes the steps of Paragraph A.

E. A method for providing a molecular efficacy of a ligand, the method comprising
  detecting an effective rate of generating $G_s(GTP)$ from $G_s(GDP)$ provided by the ligand ("ligand effective rate"); and
  detecting an apparent $EC_{50}$ for GDP binding of the ligand ("ligand $EC_{50}$");
  wherein
    a value greater than 1.0 for the product of $\eta_1$ and $\eta_2$ indicates the ligand is more efficacious than adrenaline;
    $\eta_1$ is the ligand effective rate normalized to an effective rate of adrenaline in generating $G_s(GTP)$ from $G_s(GDP)$;
    $\eta_2$ is the ligand $EC_{50}$ normalized to an apparent $EC_{50}$ for GDP binding of adrenaline; and
    a value greater than 1.0 for the product of $\eta_1$ and $\eta_2$ indicates the ligand is more efficacious than adrenaline.

F. The method of Paragraph E, wherein detecting an effective rate of generating $G_s(GTP)$ from $G_s(GDP)$ provided by the ligand comprises single-molecule fluorescence resonance energy transfer ("smFRET") imaging.

G. The method of Paragraph E or Paragraph F, wherein detecting the apparent $EC_{50}$ for GDP binding of the ligand comprises smFRET imaging.

H. The method of any one of Paragraphs E-G, wherein the method further comprises detecting the effective rate of adrenaline in generating $G_s$(GTP) from $G_s$(GDP).

I. The method of Paragraph H, wherein detecting the effective rate of adrenaline in generating $G_s$(GTP) from $G_s$(GDP) comprises smFRET imaging.

J. The method of any of Paragraphs E-I, wherein the method further comprises detecting the apparent $EC_{50}$ for GDP binding of adrenaline.

K. The method of Paragraph J, wherein detecting the apparent $EC_{50}$ for GDP binding of adrenaline comprises smFRET imaging.

L. The method of any one of Paragraphs A-D or any one of Paragraphs E-K, wherein the method comprises a β$_2$AR labelled with a compound according to the following formula ("Cy3B*-labelled β$_2$AR") wherein
$R^{101}$ is $O-R^{102}$, $O-(C_1-C_6$ alkylene)-$R^{102}$, $NH-R^{102}$, $NH-(C_1-C_{12}$ alkylene)-$NH-R^{102}$, or $NH-(C_1-C_{12}$ alkylene)-$NH-C(O)(CH_2)_o-R^{102}$;
is 1, 2, 3, 4, 5, or 6;
$R^{102}$ is a residue of the β$_2$AR; and
$X^{101}$, $X^{102}$, and $X^{103}$ are each independently H or a lone pair of electrons (i.e. providing an oxygen anion).

M. The method of Paragraph L, wherein the β$_2$AR is a mutant of native β$_2$AR.

N. The method of Paragraph L or Paragraph M, wherein the β$_2$AR is a mutant of native β$_2$AR that comprises replacing an amino acid of native β$_2$AR with a cysteine.

O. The method of any one of Paragraphs L-N, wherein the β$_2$AR is a mutant of native β$_2$AR that comprises replacing N148 of native β$_2$AR with a cysteine.

P. The method of any one of Paragraphs L-O, wherein the β$_2$AR is a mutant of native β$_2$AR that comprises replacing L266 of native β$_2$AR with a cysteine.

Q. The method of any one of Paragraphs L-P, wherein $R^{102}$ is S of a cysteine residue side chain of the β$_2$AR.

R. The method of any one of Paragraphs A-D and L-Q, or of any one of Paragraphs E-Q, wherein the method comprises a β$_2$AR labelled with a compound according to the following formula ("Cy7*-labelled β$_2$AR"), wherein
$R^{103}$ is $O-R^{104}$, $O-(C_1-C_6$ alkylene)-$R^{104}$, $NH-R^{104}$, $NH-(C_1-C_{12}$ alkylene)-$NH-R^{104}$, or $NH-(C_1-C_{12}$ alkylene)-$NH-C(O)(CH_2)_o-R^{104}$;
p is 1, 2, 3, 4, 5, or 6;
$R^{104}$ is a residue of the β$_2$AR; and
$X^{104}$, $X^{105}$, $X^{106}$, and $X^{107}$ are each independently H or a lone pair of electrons (i.e. providing an oxygen anion).

S. The method of Paragraph R, wherein the β$_2$AR is a mutant of native β$_2$AR.

T. The method of Paragraph R or Paragraph S, wherein the β$_2$AR is a mutant of native β$_2$AR that comprises replacing an amino acid of native β$_2$AR with a cysteine.

U. The method of any one of Paragraphs R-T, wherein the β$_2$AR is a mutant of native β$_2$AR that comprises replacing N148 of native β$_2$AR with a cysteine.

V. The method of any one of Paragraphs R-U, wherein the β$_2$AR is a mutant of native β$_2$AR that comprises replacing L266 of native β$_2$AR with a cysteine.

W. The method of any one of Paragraphs R-V, wherein $R^{104}$ is S of a cysteine residue side chain of the β$_2$AR.

X. The method of any one of Paragraphs A-D and L-W, or of any one of Paragraphs E-W, wherein the method comprises a β$_2$AR that is Cy3B*-labelled and Cy7*-labelled ("Cy3B*/Cy7*-labelled β$_2$AR").

Y. The method of any one of Paragraphs A-D and L-X, or of any one of Paragraphs E-X, wherein the method comprises
single-molecule fluorescence resonance energy transfer ("smFRET") imaging of a complex of $G_s$ with Cy3B*/Cy7*-labelled β$_2$AR in the presence of a saturating concentration of the ligand, a concentration of $G_s$, and a concentration of apyrase.

Z. The method of Paragraph X or Paragraph Y, wherein the method comprises
smFRET of Cy3B*/Cy7*-labelled β$_2$AR in the presence of a saturating concentration of the ligand, a concentration of GDP, and two or more different concentrations of $G_s$;
wherein at least two of the two or more different concentrations of $G_s$ are each below a saturating concentration of $G_s$.

AA. The method of any one of Paragraphs E-Z, wherein the method comprises
single-molecule fluorescence resonance energy transfer ("smFRET") imaging of a complex of $G_s$ with Cy3B*/Cy7*-labelled β$_2$Δ6-N148C/L266C in the presence of a saturating concentration of the ligand, a concentration of $G_s$, and a concentration of apyrase.

AB. The method of any one of Paragraphs E-Z, wherein the method comprises
smFRET of Cy3B*/Cy7*-labelled $\beta_2\Delta6$-N148C/L266C in the presence of a saturating concentration of the ligand, a concentration of GDP, and two or more different concentrations of $G_s$;
wherein at least two of the two or more different concentrations of $G_s$ are each below a saturating concentration of $G_s$.

AC. A compound useful in single-molecule fluorescence resonance energy transfer ("smFRET") imaging, wherein the compound is

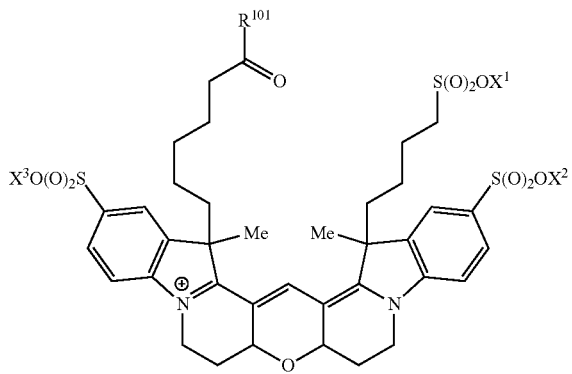

or a pharmaceutically acceptable salt and/or solvate thereof, wherein
$R^1$ is OH, O$^-$, O—($C_1$-$C_6$ alkyl), $NH_2$, NH—($C_1$-$C_{12}$ alkylene)-$NH_2$, or NH—($C_1$-$C_{12}$ alkylene)-NH—$C(O)(CH_2)_n$—$R^2$;
n is 1, 2, 3, 4, 5, or 6;
$R^2$ is Cl, Br, or I; and
$X^1$, $X^2$, and $X^3$ are each independently H or a lone pair of electrons (i.e. providing an oxygen anion).

AD. A compound useful in single-molecule fluorescence resonance energy transfer ("smFRET") imaging, wherein the compound is

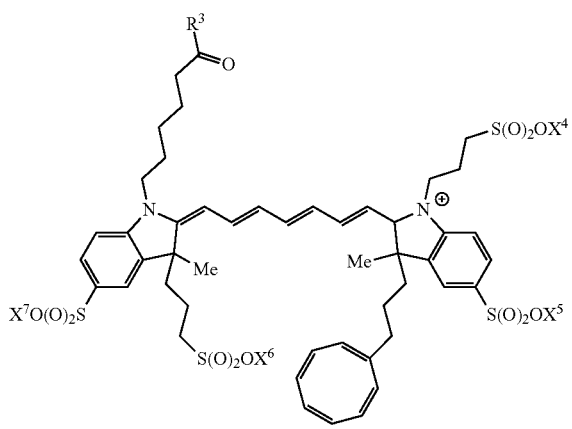

or a pharmaceutically acceptable salt and/or solvate thereof, wherein
$R^3$ is OH, O$^-$, O—($C_1$-$C_6$ alkyl), $NH_2$, NH—($C_1$-$C_{12}$ alkylene)-$NH_2$, or NH—($C_1$-$C_{12}$ alkylene)-NH—$C(O)(CH_2)_m$—$R^4$;

m is 1, 2, 3, 4, 5, or 6;
$R^4$ is Cl, Br, or I; and
$X^4$, $X^5$, $X^6$, and $X^7$ are each independently H or a lone pair of electrons (i.e. providing an oxygen anion).

Other embodiments are set forth in the following claims, along with the full scope of equivalents to which such claims are entitled.

What is claimed is:

1. A method for determining a molecular efficacy of a ligand, the method comprising:
obtaining a labelled beta-2 adrenergic receptor ($\beta_2AR$) and contacting the labelled $\beta_2AR$ with the ligand;
detecting an effective rate of generating $G_s(GTP)$ from $G_s(GDP)$ provided by the ligand ("ligand effective rate"); and
detecting an apparent $EC_{50}$ for GDP binding of the ligand ("ligand $EC_{50}$");
wherein
$\eta_1$ is the ligand effective rate normalized to an effective rate of adrenaline in generating $G_s(GTP)$ from $G_s(GDP)$;
$\eta_2$ is the ligand $EC_{50}$ normalized to an apparent $EC_{50}$ for GDP binding of adrenaline; and
a value greater than 1.0 for the product of $\eta_1$ and $\eta_2$ indicates the ligand is more efficacious than adrenaline.

2. The method of claim 1, wherein detecting an effective rate of generating $G_s(GTP)$ from $G_s(GDP)$ provided by the ligand comprises single-molecule fluorescence resonance energy transfer ("smFRET") imaging.

3. The method of claim 1, wherein detecting the apparent $EC_{50}$ for GDP binding of the ligand comprises smFRET imaging.

4. The method of claim 1, wherein the method further comprises detecting the effective rate of adrenaline in generating $G_s(GTP)$ from $G_s(GDP)$.

5. The method of claim 4, wherein detecting the effective rate of adrenaline in generating $G_s(GTP)$ from $G_s(GDP)$ comprises smFRET imaging.

6. The method of claim 1, wherein the method further comprises detecting the apparent $EC_{50}$ for GDP binding of adrenaline.

7. The method of claim 6, wherein detecting the apparent $EC_{50}$ for GDP binding of adrenaline comprises smFRET imaging.

8. The method of claim 1, wherein the labelled $\beta_2AR$ is labelled with a compound according to the following formula

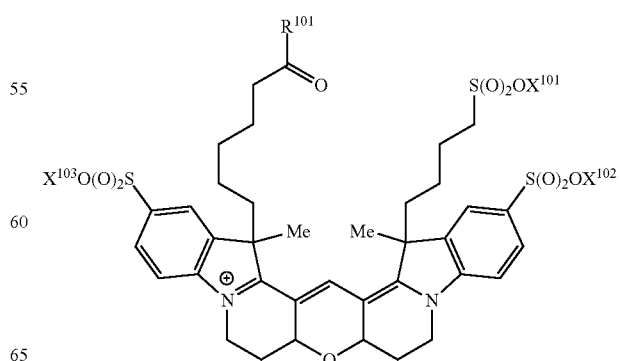

("Cy3B*-labelled $\beta_2$AR") wherein
$R^{101}$ is $O—R^{102}$, $O—(C_1-C_6$ alkylene$)-R^{102}$, $NH—R^{102}$, $NH—(C_1-C_{12}$ alkylene$)-NH—R^{102}$; or $NH—(C_1-C_{12}$ alkylene$)-NH—C(O)(CH_2)_o—R^{102}$;
o is 1, 2, 3, 4, 5, or 6;
$R^{102}$ is a residue of the $\beta_2$AR; and
$X^{101}, X^{102}$, and $X^{103}$ are each independently H or a lone pair of electrons.

9. The method of claim 8, wherein the $\beta_2$AR is a mutant of native $\beta_2$AR that comprises replacing an amino acid of native $\beta_2$AR with a cysteine.

10. The method of claim 1, wherein the labelled $\beta_2$AR is labelled with a compound according to the following formula

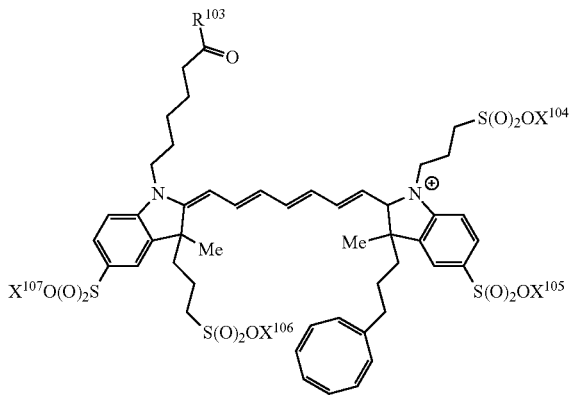

("Cy7*-labelled $\beta_2$AR"), wherein
$R^{103}$ is $O—R^{104}$, $O—(C_1-C_6$ alkylene$)-R^{104}$, $NH—R^{104}$, $NH—(C_1-C_{12}$ alkylene$)-NH—R^{104}$, or $NH—(C_1-C_{12}$ alkylene$)-NH—C(O)(CH_2)_o—R^{104}$;
p is 1, 2, 3, 4, 5, or 6;
$R^{104}$ is a residue of the $\beta_2$AR; and
$X^{104}, X^{105}, X^{106}$, and $X^{107}$ are each independently H or a lone pair of electrons.

11. The method of claim 10, wherein the $\beta_2$AR is a mutant of native $\beta_2$AR that comprises replacing an amino acid of native $\beta_2$AR with a cysteine.

12. The method of claim 10, wherein the method comprises a $\beta_2$AR that is Cy3B*-labelled and Cy7*-labelled ("Cy3B*/Cy7*-labelled $\beta_2$AR").

13. The method of claim 12, wherein the method comprises
single-molecule fluorescence resonance energy transfer ("smFRET") imaging of a complex of $G_s$ with Cy3B*/Cy7*-labelled $\beta_2$AR in the presence of a saturating concentration of the ligand, a concentration of $G_s$, and a concentration of apyrase.

14. The method of claim 12, wherein the method comprises
smFRET of Cy3B*/Cy7*-labelled $\beta_2$AR in the presence of a saturating concentration of the ligand, a concentration of GDP, and two or more different concentrations of $G_s$;
wherein at least two of the two or more different concentrations of $G_s$ are each below a saturating concentration of $G_s$.

15. The method of claim 12, wherein the method comprises
single-molecule fluorescence resonance energy transfer ("smFRET") imaging of a complex of $G_s$ with Cy3B*/Cy7*-labelled $\beta_2\Delta$6-N148C/L266C in the presence of a saturating concentration of the ligand, a concentration of $G_s$, and a concentration of apyrase.

16. The method of claim 15, wherein the method comprises
smFRET of Cy3B*/Cy7*-labelled $\beta_2\Delta$6-N148C/L266C in the presence of a saturating concentration of the ligand, a concentration of GDP, and two or more different concentrations of $G_s$;
wherein at least two of the two or more different concentrations of $G_s$ are each below a saturating concentration of $G_s$.

* * * * *